United States Patent [19]
Litwack et al.

[11] Patent Number: 5,856,169
[45] Date of Patent: Jan. 5, 1999

[54] ISOFORMS OF HUMAN INTERLEUKIN-1β CONVERTING ENZYME AND METHODS OF USING THE SAME

[75] Inventors: Gerald Litwack, Bryn Mawr; Emad S. Alnemri; Teresa Fernandez-Alnemri, both of Ambler, all of Pa.

[73] Assignee: Thomas Jefferson University, Philadelphia, Pa.

[21] Appl. No.: 391,916

[22] Filed: Feb. 21, 1995

[51] Int. Cl.⁶ .............................. C12N 1/21; C12N 5/10; C12N 15/63; C07H 21/04
[52] U.S. Cl. ..................................... 435/252.3; 435/320.1; 435/325; 536/23.2; 536/24.31; 536/24.33
[58] Field of Search ............................. 435/252.3, 320.1, 435/325; 536/23.2, 24.31, 24.33

[56] References Cited

U.S. PATENT DOCUMENTS

| | | | |
|---|---|---|---|
| 5,278,061 | 1/1994 | Bull et al. | 435/212 |
| 5,416,013 | 5/1995 | Black et al. | 435/226 |
| 5,492,824 | 2/1996 | Talanian et al. | 435/226 |

FOREIGN PATENT DOCUMENTS

| | | |
|---|---|---|
| 2076159 | 2/1993 | Canada . |
| 93/15207 | 8/1993 | WIPO . |

OTHER PUBLICATIONS

Alnemri, E. et al., "Cloning and Expression of Four Novel Isoforms of Human Interleukin–1β Converting Enzyme with Different Apoptotic Activities", *The J. of Biol. Chem.* 1995, 270(9), 4312–4317.

Sambrook J. et al. Molecular Cloning, A Laboratory Manual, Second Edition. Cold Spring Harbor Laboratory Press. 1989, p. 14.15.

Alnemri, E., et al. "Overexpressed Full–Length Human BCL2 Extends the Survival of Baculovirus–Infected Sf9 Insect Cells", *PNAS USA* 1992, 89, 7295–7299.

Alnemri, E. et al., "Characterization and Purification of a Functional Rat Glucocorticoid Receptor Overexpressed in a Baculovirus System", *The Journal of Biol. Chem.* 266(6), 3925–3936.

Black, R. et al., "Activation of Interleukin–1β By a Co–Induced Protease", *FEBS Letters* 1989, 247(2), 386–390.

Cerretti, D. et al., "Molecular Cloning of the Interleukin–1β Converting Enzyme", *Science* 1992, 256, 97–100.

Cerretti, D. et al., "Molecular Characterization of the Gene for Human Interleukin–1β Converting Enzyme (1L1BC)", *Genomics* 1994, 20, 468–473.

Gagliardini, V. et al., "Prevention of Vertebrate Neuronal Death by the crmA Gene", *Science* 1994, 263, 826–828.

Griffin, W.S. et al, "Brain Interleukin 1 and S–100 Immunoreactivity are Elevated in Down Syndrome and Alzheimer Disease", *PNAS USA* 1989, 86, 7611–7615.

Howard, A. et al., "IL–1–Converting Enzyme Requires Aspartic Acid Residues for Processing of the IL–1β Precursor at Two Distinct Sites and Does Not Cleave 31–kDa IL–1α", *J. of Immunol.* 1991, 174(9), 2964–2969.

Kostura, M. et al., "Identification of a Monocyte Specific Pre–Interleukin 1β Convertase Activity", *PNAS USA* 1989, 86, 5227–5231.

Kumar, S. et al., "Induction of Apoptosis by the Mouse Nedd2 Gene, Which Encodes a Protein Similar to the Product of the Caenorhabditis elegans Cell Death Gene ced–3 and the Mammalian IL–1β–Converting Enzyme", *Genes & Development* 1994, 8, 1613–1626.

Miura, M. et al., "Induction of Apoptosis in Fibroblasts by IL–1β–Converting Enzyme, a Mammalian Homolog of the C. elegans Cell Death Gene ced–3," *Cell* 1993, 75, 653–660.

Ray, C. et al., "Viral Inhibition of Inflammation: Cowpox Virus Encodes an Inhibitor of the Interleukin 1β Converting Enzyme", *Cell* 1992, 69, 597–604.

Sleath, P. et al., "Substrate Specificity of the Protease That Processes Human Interleukin–1β*", *The J. of Biol. Chem.* 1990, 265(24), 14526–14528.

Thornberry, N. et al., "A Novel Heterodimeric Cysteine Protease is Required for Interleukin–1β Processing in Monocytes", *Nature* 1992, 356, 768–774.

Walker, N.P.C. et al., "Crystal Structure of the Cysteine Protease Interleukin–1β–Converting Enzyme: A (p20/p10)₂ Homodimer", *Cell* 1994, 78, 343–352.

Wilson, K. et al., "Structure and Mechanism of Interleukin–1β Converting Enyme", *Nature* 1994, 370, 270–275.

Yuan, J. et al., "The C. elegans Cell Death Gene ced–3 Encodes a Protein Similar to Mammalian Interleukin–1β–Converting Enzyme", *Cell* 1993, 75, 641–652.

Li, P. et al., "Mice Deficient in IL–1β–Converting Enzyme Are Defective in Production of Mature IL–1β and Resistant to Endotoxic Shock", *Cell* 1995, 80, 401–411.

*Primary Examiner*—Kawai Lau
*Attorney, Agent, or Firm*—Seed and Berry LLP

[57] ABSTRACT

Substantially pure interleukin-1 converting enzyme isoforms are disclosed. Pharmaceutical compositions comprising one or more interleukin-1 converting enzyme isoforms are disclosed. Nucleic acid molecules that encode interleukin-1 converting enzyme isoforms, recombinant expression vectors that comprise a nucleic acid sequence that encodes an interleukin-1 converting enzyme isoform, and host cells that comprise recombinant expression vectors that comprise nucleic acid sequences that encode interleukin-1 converting enzyme isoforms are disclosed. Fragments of nucleic acid molecules with sequences encoding interleukin-1 converting enzyme isoform and oligonucleotide molecules that comprise a nucleotide sequence complimentary to fragment of a nucleotide sequence that encodes an interleukin-1 converting enzyme isoform are disclosed. Antibodies which bind to an epitope on interleukin-1 converting enzyme isoforms are disclosed. Methods of identifying inhibitors of ICE isoforms are disclosed.

31 Claims, No Drawings

SEQUENCE LISTING ( 1 ) GENERAL INFORMATION:

( i i i ) NUMBER OF SEQUENCES: 25

( 2 ) INFORMATION FOR SEQ ID NO:1:

( i ) SEQUENCE CHARACTERISTICS:
        ( A ) LENGTH: 1248 base pairs
        ( B ) TYPE: nucleic acid
        ( C ) STRANDEDNESS: double
        ( D ) TOPOLOGY: linear ( i i ) MOLECULE TYPE: cDNA ( i x ) FEATURE:
        ( A ) NAME/KEY: CDS
        ( B ) LOCATION: 1..1212

( x i ) SEQUENCE DESCRIPTION: SEQ ID NO:1:

```
ATG GCC GAC AAG GTC CTG AAG GAG AAG AGA AAG CTG TTT ATC CGT TCC        48
Met Ala Asp Lys Val Leu Lys Glu Lys Arg Lys Leu Phe Ile Arg Ser
 1               5                  10                  15

ATG GGT GAA GGT ACA ATA AAT GGC TTA CTG GAT GAA TTA TTA CAG ACA        96
Met Gly Glu Gly Thr Ile Asn Gly Leu Leu Asp Glu Leu Leu Gln Thr
                20                  25                  30

AGG GTG CTG AAC AAG GAA GAG ATG GAG AAA GTA AAA CGT GAA AAT GCT       144
Arg Val Leu Asn Lys Glu Glu Met Glu Lys Val Lys Arg Glu Asn Ala
                    35                  40                  45

ACA GTT ATG GAT AAG ACC CGA GCT TTG ATT GAC TCC GTT ATT CCG AAA       192
Thr Val Met Asp Lys Thr Arg Ala Leu Ile Asp Ser Val Ile Pro Lys
             50                  55                  60

GGG GCA CAG GCA TGC CAA ATT TGC ATC ACA TAC ATT TGT GAA GAA GAC       240
Gly Ala Gln Ala Cys Gln Ile Cys Ile Thr Tyr Ile Cys Glu Glu Asp
 65                  70                  75                  80

AGT TAC CTG GCA GGG ACG CTG GGA CTC TCA GCA GAT CAA ACA TCT GGA       288
Ser Tyr Leu Ala Gly Thr Leu Gly Leu Ser Ala Asp Gln Thr Ser Gly
                     85                  90                  95

AAT TAC CTT AAT ATG CAA GAC TCT CAA GGA GTA CTT TCT TCC TTT CCA       336
Asn Tyr Leu Asn Met Gln Asp Ser Gln Gly Val Leu Ser Ser Phe Pro
                100                 105                 110

GCT CCT CAG GCA GTG CAG GAC AAC CCA GCT ATG CCC ACA TCC TCA GGC       384
Ala Pro Gln Ala Val Gln Asp Asn Pro Ala Met Pro Thr Ser Ser Gly
            115                 120                 125

TCA GAA GGG AAT GTC AAG CTT TGC TCC CTA GAA GAA GCT CAA AGG ATA       432
Ser Glu Gly Asn Val Lys Leu Cys Ser Leu Glu Glu Ala Gln Arg Ile
        130                 135                 140

TGG AAA CAA AAG TCG GCA GAG ATT TAT CCA ATA ATG GAC AAG TCA AGC       480
Trp Lys Gln Lys Ser Ala Glu Ile Tyr Pro Ile Met Asp Lys Ser Ser
145                 150                 155                 160

CGC ACA CGT CTT GCT CTC ATT ATC TGC AAT GAA GAA TTT GAC AGT ATT       528
Arg Thr Arg Leu Ala Leu Ile Ile Cys Asn Glu Glu Phe Asp Ser Ile
                    165                 170                 175

CCT AGA AGA ACT GGA GCT GAG GTT GAC ATC ACA GGC ATG ACA ATG CTG       576
Pro Arg Arg Thr Gly Ala Glu Val Asp Ile Thr Gly Met Thr Met Leu
                180                 185                 190

CTA CAA AAT CTG GGG TAC AGC GTA GAT GTG AAA AAA AAT CTC ACT GCT       624
Leu Gln Asn Leu Gly Tyr Ser Val Asp Val Lys Lys Asn Leu Thr Ala
            195                 200                 205

TCG GAC ATG ACT ACA GAG CTG GAG GCA TTT GCA CAC CGC CCA GAG CAC       672
Ser Asp Met Thr Thr Glu Leu Glu Ala Phe Ala His Arg Pro Glu His
        210                 215                 220
```

| | | | | | | | | | | | | | | | | |
|---|---|---|---|---|---|---|---|---|---|---|---|---|---|---|---|---|
| AAG | ACC | TCT | GAC | AGC | ACG | TTC | CTG | GTG | TTC | ATG | TCT | CAT | GGT | ATT | CGG | 720 |
| Lys | Thr | Ser | Asp | Ser | Thr | Phe | Leu | Val | Phe | Met | Ser | His | Gly | Ile | Arg | |
| 225 | | | | | 230 | | | | | 235 | | | | | 240 | |
| GAA | GGC | ATT | TGT | GGG | AAG | AAA | CAC | TCT | GAG | CAA | GTC | CCA | GAT | ATA | CTA | 768 |
| Glu | Gly | Ile | Cys | Gly | Lys | Lys | His | Ser | Glu | Gln | Val | Pro | Asp | Ile | Leu | |
| | | | | 245 | | | | | 250 | | | | | 255 | | |
| CAA | CTC | AAT | GCA | ATC | TTT | AAC | ATG | TTG | AAT | ACC | AAG | AAC | TGC | CCA | AGT | 816 |
| Gln | Leu | Asn | Ala | Ile | Phe | Asn | Met | Leu | Asn | Thr | Lys | Asn | Cys | Pro | Ser | |
| | | | 260 | | | | | 265 | | | | | 270 | | | |
| TTG | AAG | GAC | AAA | CCG | AAG | GTG | ATC | ATC | ATC | CAG | GCC | TGC | CGT | GGT | GAC | 864 |
| Leu | Lys | Asp | Lys | Pro | Lys | Val | Ile | Ile | Ile | Gln | Ala | Cys | Arg | Gly | Asp | |
| | | 275 | | | | | 280 | | | | | 285 | | | | |
| AGC | CCT | GGT | GTG | GTG | TGG | TTT | AAA | GAT | TCA | GTA | GGA | GTT | TCT | GGA | AAC | 912 |
| Ser | Pro | Gly | Val | Val | Trp | Phe | Lys | Asp | Ser | Val | Gly | Val | Ser | Gly | Asn | |
| | 290 | | | | | 295 | | | | | 300 | | | | | |
| CTA | TCT | TTA | CCA | ACT | ACA | GAA | GAG | TTT | GAG | GAT | GAT | GCT | ATT | AAG | AAA | 960 |
| Leu | Ser | Leu | Pro | Thr | Thr | Glu | Glu | Phe | Glu | Asp | Asp | Ala | Ile | Lys | Lys | |
| 305 | | | | | 310 | | | | | 315 | | | | | 320 | |
| GCC | CAC | ATA | GAG | AAG | GAT | TTT | ATC | GCT | TTC | TGC | TCT | TCC | ACA | CCA | GAT | 1008 |
| Ala | His | Ile | Glu | Lys | Asp | Phe | Ile | Ala | Phe | Cys | Ser | Ser | Thr | Pro | Asp | |
| | | | | 325 | | | | | 330 | | | | | 335 | | |
| AAT | GTT | TCT | TGG | AGA | CAT | CCC | ACA | ATG | GGC | TCT | GTT | TTT | ATT | GGA | AGA | 1056 |
| Asn | Val | Ser | Trp | Arg | His | Pro | Thr | Met | Gly | Ser | Val | Phe | Ile | Gly | Arg | |
| | | | 340 | | | | | 345 | | | | | 350 | | | |
| CTC | ATT | GAA | CAT | ATG | CAA | GAA | TAT | GCC | TGT | TCC | TGT | GAT | GTG | GAG | GAA | 1104 |
| Leu | Ile | Glu | His | Met | Gln | Glu | Tyr | Ala | Cys | Ser | Cys | Asp | Val | Glu | Glu | |
| | | 355 | | | | | 360 | | | | | 365 | | | | |
| ATT | TTC | CGC | AAG | GTT | CGA | TTT | TCA | TTT | GAG | CAG | CCA | GAT | GGT | AGA | GCG | 1152 |
| Ile | Phe | Arg | Lys | Val | Arg | Phe | Ser | Phe | Glu | Gln | Pro | Asp | Gly | Arg | Ala | |
| | 370 | | | | | 375 | | | | | 380 | | | | | |
| CAG | ATG | CCC | ACC | ACT | GAA | AGA | GTG | ACT | TTG | ACA | AGA | TGT | TTC | TAC | CTC | 1200 |
| Gln | Met | Pro | Thr | Thr | Glu | Arg | Val | Thr | Leu | Thr | Arg | Cys | Phe | Tyr | Leu | |
| 385 | | | | | 390 | | | | | 395 | | | | | 400 | |
| TTC | CCA | GGA | CAT | TAAAATAAGG | | AAACTGTATG | | AATGTCTGCG | | GGCAGG | | | | | | 1248 |
| Phe | Pro | Gly | His | | | | | | | | | | | | | |

( 2 ) INFORMATION FOR SEQ ID NO:2:

( i ) SEQUENCE CHARACTERISTICS:
        ( A ) LENGTH: 404 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

| | | | | | | | | | | | | | | |
|---|---|---|---|---|---|---|---|---|---|---|---|---|---|---|
| Met | Ala | Asp | Lys | Val | Leu | Lys | Glu | Lys | Arg | Lys | Leu | Phe | Ile | Arg | Ser |
| 1 | | | | 5 | | | | | 10 | | | | | 15 | |
| Met | Gly | Glu | Gly | Thr | Ile | Asn | Gly | Leu | Leu | Asp | Glu | Leu | Leu | Gln | Thr |
| | | | 20 | | | | | 25 | | | | | 30 | | |
| Arg | Val | Leu | Asn | Lys | Glu | Glu | Met | Glu | Lys | Val | Lys | Arg | Glu | Asn | Ala |
| | | 35 | | | | | 40 | | | | | 45 | | | |
| Thr | Val | Met | Asp | Lys | Thr | Arg | Ala | Leu | Ile | Asp | Ser | Val | Ile | Pro | Lys |
| | 50 | | | | | 55 | | | | | 60 | | | | |
| Gly | Ala | Gln | Ala | Cys | Gln | Ile | Cys | Ile | Thr | Tyr | Ile | Cys | Glu | Glu | Asp |
| 65 | | | | 70 | | | | | 75 | | | | | 80 | |
| Ser | Tyr | Leu | Ala | Gly | Thr | Leu | Gly | Leu | Ser | Ala | Asp | Gln | Thr | Ser | Gly |
| | | | 85 | | | | | 90 | | | | | 95 | | |
| Asn | Tyr | Leu | Asn | Met | Gln | Asp | Ser | Gln | Gly | Val | Leu | Ser | Ser | Phe | Pro |
| | | | 100 | | | | | 105 | | | | | 110 | | |

-continued

| Ala | Pro | Gln | Ala | Val | Gln | Asp | Asn | Pro | Ala | Met | Pro | Thr | Ser | Ser | Gly |
|  |  | 115 |  |  |  | 120 |  |  |  |  | 125 |  |  |  |  |

| Ser | Glu | Gly | Asn | Val | Lys | Leu | Cys | Ser | Leu | Glu | Glu | Ala | Gln | Arg | Ile |
|  | 130 |  |  |  |  | 135 |  |  |  | 140 |  |  |  |  |  |

| Trp | Lys | Gln | Lys | Ser | Ala | Glu | Ile | Tyr | Pro | Ile | Met | Asp | Lys | Ser | Ser |
| 145 |  |  |  |  | 150 |  |  |  |  | 155 |  |  |  |  | 160 |

| Arg | Thr | Arg | Leu | Ala | Leu | Ile | Ile | Cys | Asn | Glu | Glu | Phe | Asp | Ser | Ile |
|  |  |  |  | 165 |  |  |  |  | 170 |  |  |  |  | 175 |  |

| Pro | Arg | Arg | Thr | Gly | Ala | Glu | Val | Asp | Ile | Thr | Gly | Met | Thr | Met | Leu |
|  |  |  | 180 |  |  |  |  | 185 |  |  |  |  | 190 |  |  |

| Leu | Gln | Asn | Leu | Gly | Tyr | Ser | Val | Asp | Val | Lys | Lys | Asn | Leu | Thr | Ala |
|  |  | 195 |  |  |  |  | 200 |  |  |  |  | 205 |  |  |  |

| Ser | Asp | Met | Thr | Thr | Glu | Leu | Glu | Ala | Phe | Ala | His | Arg | Pro | Glu | His |
|  | 210 |  |  |  |  | 215 |  |  |  |  | 220 |  |  |  |  |

| Lys | Thr | Ser | Asp | Ser | Thr | Phe | Leu | Val | Phe | Met | Ser | His | Gly | Ile | Arg |
| 225 |  |  |  |  | 230 |  |  |  |  | 235 |  |  |  |  | 240 |

| Glu | Gly | Ile | Cys | Gly | Lys | Lys | His | Ser | Glu | Gln | Val | Pro | Asp | Ile | Leu |
|  |  |  |  | 245 |  |  |  |  | 250 |  |  |  |  | 255 |  |

| Gln | Leu | Asn | Ala | Ile | Phe | Asn | Met | Leu | Asn | Thr | Lys | Asn | Cys | Pro | Ser |
|  |  |  | 260 |  |  |  |  | 265 |  |  |  |  | 270 |  |  |

| Leu | Lys | Asp | Lys | Pro | Lys | Val | Ile | Ile | Ile | Gln | Ala | Cys | Arg | Gly | Asp |
|  |  | 275 |  |  |  |  | 280 |  |  |  |  | 285 |  |  |  |

| Ser | Pro | Gly | Val | Val | Trp | Phe | Lys | Asp | Ser | Val | Gly | Val | Ser | Gly | Asn |
|  | 290 |  |  |  |  | 295 |  |  |  |  | 300 |  |  |  |  |

| Leu | Ser | Leu | Pro | Thr | Thr | Glu | Glu | Phe | Glu | Asp | Asp | Ala | Ile | Lys | Lys |
| 305 |  |  |  |  | 310 |  |  |  |  | 315 |  |  |  |  | 320 |

| Ala | His | Ile | Glu | Lys | Asp | Phe | Ile | Ala | Phe | Cys | Ser | Ser | Thr | Pro | Asp |
|  |  |  |  | 325 |  |  |  |  | 330 |  |  |  |  | 335 |  |

| Asn | Val | Ser | Trp | Arg | His | Pro | Thr | Met | Gly | Ser | Val | Phe | Ile | Gly | Arg |
|  |  |  | 340 |  |  |  |  | 345 |  |  |  |  | 350 |  |  |

| Leu | Ile | Glu | His | Met | Gln | Glu | Tyr | Ala | Cys | Ser | Cys | Asp | Val | Glu | Glu |
|  |  | 355 |  |  |  |  | 360 |  |  |  |  | 365 |  |  |  |

| Ile | Phe | Arg | Lys | Val | Arg | Phe | Ser | Phe | Glu | Gln | Pro | Asp | Gly | Arg | Ala |
|  | 370 |  |  |  |  | 375 |  |  |  |  | 380 |  |  |  |  |

| Gln | Met | Pro | Thr | Thr | Glu | Arg | Val | Thr | Leu | Thr | Arg | Cys | Phe | Tyr | Leu |
| 385 |  |  |  |  | 390 |  |  |  |  | 395 |  |  |  |  | 400 |

| Phe | Pro | Gly | His |

(2) INFORMATION FOR SEQ ID NO:3:

(i) SEQUENCE CHARACTERISTICS:
        (A) LENGTH: 1185 base pairs
        (B) TYPE: nucleic acid
        (C) STRANDEDNESS: double
        (D) TOPOLOGY: linear (ii) MOLECULE TYPE: cDNA (ix) FEATURE:
        (A) NAME/KEY: CDS
        (B) LOCATION: 1..1149

(xi) SEQUENCE DESCRIPTION: SEQ ID NO:3:

| ATG | GCC | GAC | AAG | GTC | CTG | AAG | GAG | AAG | AGA | AAG | CTG | TTT | ATC | CGT | TCC | 48 |
| Met | Ala | Asp | Lys | Val | Leu | Lys | Glu | Lys | Arg | Lys | Leu | Phe | Ile | Arg | Ser |  |
| 1 |  |  |  | 5 |  |  |  |  | 10 |  |  |  |  | 15 |  |  |

| ATG | GGT | GAA | GGT | ACA | ATA | AAT | GGC | TTA | CTG | GAT | GAA | TTA | TTA | CAG | ACA | 96 |
| Met | Gly | Glu | Gly | Thr | Ile | Asn | Gly | Leu | Leu | Asp | Glu | Leu | Leu | Gln | Thr |  |
|  |  |  | 20 |  |  |  |  | 25 |  |  |  |  | 30 |  |  |  |

| | | | | | | | | | | | | | | | | |
|---|---|---|---|---|---|---|---|---|---|---|---|---|---|---|---|---|
| AGG | GTG | CTG | AAC | AAG | GAA | GAG | ATG | GAG | AAA | GTA | AAA | CGT | GAA | AAT | GCT | 144 |
| Arg | Val | Leu | Asn | Lys | Glu | Glu | Met | Glu | Lys | Val | Lys | Arg | Glu | Asn | Ala | |
| | | 35 | | | | | 40 | | | | | 45 | | | | |
| ACA | GTT | ATG | GAT | AAG | ACC | CGA | GCT | TTG | ATT | GAC | TCC | GTT | ATT | CCG | AAA | 192 |
| Thr | Val | Met | Asp | Lys | Thr | Arg | Ala | Leu | Ile | Asp | Ser | Val | Ile | Pro | Lys | |
| | 50 | | | | | 55 | | | | | 60 | | | | | |
| GGG | GCA | CAG | GCA | TGC | CAA | ATT | TGC | ATC | ACA | TAC | ATT | TGT | GAA | GAA | GAC | 240 |
| Gly | Ala | Gln | Ala | Cys | Gln | Ile | Cys | Ile | Thr | Tyr | Ile | Cys | Glu | Glu | Asp | |
| 65 | | | | | 70 | | | | | 75 | | | | | 80 | |
| AGT | TAC | CTG | GCA | GGG | ACG | CTG | GGA | CTC | TCA | GCA | GCT | CCT | CAG | GCA | GTG | 288 |
| Ser | Tyr | Leu | Ala | Gly | Thr | Leu | Gly | Leu | Ser | Ala | Ala | Pro | Gln | Ala | Val | |
| | | | | 85 | | | | | 90 | | | | | 95 | | |
| CAG | GAC | AAC | CCA | GCT | ATG | CCC | ACA | TCC | TCA | GGC | TCA | GAA | GGG | AAT | GTC | 336 |
| Gln | Asp | Asn | Pro | Ala | Met | Pro | Thr | Ser | Ser | Gly | Ser | Glu | Gly | Asn | Val | |
| | | | 100 | | | | | 105 | | | | | 110 | | | |
| AAG | CTT | TGC | TCC | CTA | GAA | GAA | GCT | CAA | AGG | ATA | TGG | AAA | CAA | AAG | TCG | 384 |
| Lys | Leu | Cys | Ser | Leu | Glu | Glu | Ala | Gln | Arg | Ile | Trp | Lys | Gln | Lys | Ser | |
| | | | 115 | | | | | 120 | | | | | 125 | | | |
| GCA | GAG | ATT | TAT | CCA | ATA | ATG | GAC | AAG | TCA | AGC | CGC | ACA | CGT | CTT | GCT | 432 |
| Ala | Glu | Ile | Tyr | Pro | Ile | Met | Asp | Lys | Ser | Ser | Arg | Thr | Arg | Leu | Ala | |
| 130 | | | | | 135 | | | | | 140 | | | | | | |
| CTC | ATT | ATC | TGC | AAT | GAA | GAA | TTT | GAC | AGT | ATT | CCT | AGA | AGA | ACT | GGA | 480 |
| Leu | Ile | Ile | Cys | Asn | Glu | Glu | Phe | Asp | Ser | Ile | Pro | Arg | Arg | Thr | Gly | |
| 145 | | | | | 150 | | | | | 155 | | | | | 160 | |
| GCT | GAG | GTT | GAC | ATC | ACA | GGC | ATG | ACA | ATG | CTG | CTA | CAA | AAT | CTG | GGG | 528 |
| Ala | Glu | Val | Asp | Ile | Thr | Gly | Met | Thr | Met | Leu | Leu | Gln | Asn | Leu | Gly | |
| | | | | 165 | | | | | 170 | | | | | 175 | | |
| TAC | AGC | GTA | GAT | GTG | AAA | AAA | AAT | CTC | ACT | GCT | TCG | GAC | ATG | ACT | ACA | 576 |
| Tyr | Ser | Val | Asp | Val | Lys | Lys | Asn | Leu | Thr | Ala | Ser | Asp | Met | Thr | Thr | |
| | | | 180 | | | | | 185 | | | | | 190 | | | |
| GAG | CTG | GAG | GCA | TTT | GCA | CAC | CGC | CCA | GAG | CAC | AAG | ACC | TCT | GAC | AGC | 624 |
| Glu | Leu | Glu | Ala | Phe | Ala | His | Arg | Pro | Glu | His | Lys | Thr | Ser | Asp | Ser | |
| | | 195 | | | | | 200 | | | | | 205 | | | | |
| ACG | TTC | CTG | GTG | TTC | ATG | TCT | CAT | GGT | ATT | CGG | GAA | GGC | ATT | TGT | GGG | 672 |
| Thr | Phe | Leu | Val | Phe | Met | Ser | His | Gly | Ile | Arg | Glu | Gly | Ile | Cys | Gly | |
| | 210 | | | | | 215 | | | | | 220 | | | | | |
| AAG | AAA | CAC | TCT | GAG | CAA | GTC | CCA | GAT | ATA | CTA | CAA | CTC | AAT | GCA | ATC | 720 |
| Lys | Lys | His | Ser | Glu | Gln | Val | Pro | Asp | Ile | Leu | Gln | Leu | Asn | Ala | Ile | |
| 225 | | | | | 230 | | | | | 235 | | | | | 240 | |
| TTT | AAC | ATG | TTG | AAT | ACC | AAG | AAC | TGC | CCA | AGT | TTG | AAG | GAC | AAA | CCG | 768 |
| Phe | Asn | Met | Leu | Asn | Thr | Lys | Asn | Cys | Pro | Ser | Leu | Lys | Asp | Lys | Pro | |
| | | | | 245 | | | | | 250 | | | | | 255 | | |
| AAG | GTG | ATC | ATC | ATC | CAG | GCC | TGC | CGT | GGT | GAC | AGC | CCT | GGT | GTG | GTG | 816 |
| Lys | Val | Ile | Ile | Ile | Gln | Ala | Cys | Arg | Gly | Asp | Ser | Pro | Gly | Val | Val | |
| | | | 260 | | | | | 265 | | | | | 270 | | | |
| TGG | TTT | AAA | GAT | TCA | GTA | GGA | GTT | TCT | GGA | AAC | CTA | TCT | TTA | CCA | ACT | 864 |
| Trp | Phe | Lys | Asp | Ser | Val | Gly | Val | Ser | Gly | Asn | Leu | Ser | Leu | Pro | Thr | |
| | | 275 | | | | | 280 | | | | | 285 | | | | |
| ACA | GAA | GAG | TTT | GAG | GAT | GAT | GCT | ATT | AAG | AAA | GCC | CAC | ATA | GAG | AAG | 912 |
| Thr | Glu | Glu | Phe | Glu | Asp | Asp | Ala | Ile | Lys | Lys | Ala | His | Ile | Glu | Lys | |
| | 290 | | | | | 295 | | | | | 300 | | | | | |
| GAT | TTT | ATC | GCT | TTC | TGC | TCT | TCC | ACA | CCA | GAT | AAT | GTT | TCT | TGG | AGA | 960 |
| Asp | Phe | Ile | Ala | Phe | Cys | Ser | Ser | Thr | Pro | Asp | Asn | Val | Ser | Trp | Arg | |
| 305 | | | | | 310 | | | | | 315 | | | | | 320 | |
| CAT | CCC | ACA | ATG | GGC | TCT | GTT | TTT | ATT | GGA | AGA | CTC | ATT | GAA | CAT | ATG | 1008 |
| His | Pro | Thr | Met | Gly | Ser | Val | Phe | Ile | Gly | Arg | Leu | Ile | Glu | His | Met | |
| | | | | 325 | | | | | 330 | | | | | 335 | | |
| CAA | GAA | TAT | GCC | TGT | TCC | TGT | GAT | GTG | GAG | GAA | ATT | TTC | CGC | AAG | GTT | 1056 |
| Gln | Glu | Tyr | Ala | Cys | Ser | Cys | Asp | Val | Glu | Glu | Ile | Phe | Arg | Lys | Val | |
| | | | 340 | | | | | 345 | | | | | 350 | | | |

```
CGA   TTT   TCA   TTT   GAG   CAG   CCA   GAT   GGT   AGA   GCG   CAG   ATG   CCC   ACC   ACT     1104
Arg   Phe   Ser   Phe   Glu   Gln   Pro   Asp   Gly   Arg   Ala   Gln   Met   Pro   Thr   Thr
            355                           360                           365

GAA   AGA   GTG   ACT   TTG   ACA   AGA   TGT   TTC   TAC   CTC   TTC   CCA   GGA   CAT             1149
Glu   Arg   Val   Thr   Leu   Thr   Arg   Cys   Phe   Tyr   Leu   Phe   Pro   Gly   His
370                           375                           380

TAAAATAAGG   AAACTGTATG   AATGTCTGCG   GGCAGG                                                     1185
```

( 2 ) INFORMATION FOR SEQ ID NO:4:

( i ) SEQUENCE CHARACTERISTICS:
    ( A ) LENGTH: 383 amino acids
    ( B ) TYPE: amino acid
    ( D ) TOPOLOGY: linear ( i i ) MOLECULE TYPE: protein ( x i ) SEQUENCE DESCRIPTION: SEQ ID NO:4:

```
Met   Ala   Asp   Lys   Val   Leu   Lys   Glu   Lys   Lys   Leu   Phe   Ile   Arg   Ser
  1                       5                      10                          15

Met   Gly   Glu   Gly   Thr   Ile   Asn   Gly   Leu   Leu   Asp   Glu   Leu   Leu   Gln   Thr
                  20                            25                          30

Arg   Val   Leu   Asn   Lys   Glu   Glu   Met   Glu   Lys   Val   Lys   Arg   Glu   Asn   Ala
                  35                            40                          45

Thr   Val   Met   Asp   Lys   Thr   Arg   Ala   Leu   Ile   Asp   Ser   Val   Ile   Pro   Lys
      50                            55                            60

Gly   Ala   Gln   Ala   Cys   Gln   Ile   Cys   Ile   Thr   Tyr   Ile   Cys   Glu   Glu   Asp
 65                           70                            75                          80

Ser   Tyr   Leu   Ala   Gly   Thr   Leu   Gly   Leu   Ser   Ala   Ala   Pro   Gln   Ala   Val
                        85                            90                          95

Gln   Asp   Asn   Pro   Ala   Met   Pro   Thr   Ser   Ser   Gly   Ser   Glu   Gly   Asn   Val
                  100                           105                         110

Lys   Leu   Cys   Ser   Leu   Glu   Glu   Ala   Gln   Arg   Ile   Trp   Lys   Gln   Lys   Ser
                  115                           120                         125

Ala   Glu   Ile   Tyr   Pro   Ile   Met   Asp   Lys   Ser   Ser   Arg   Thr   Arg   Leu   Ala
            130                           135                         140

Leu   Ile   Ile   Cys   Asn   Glu   Glu   Phe   Asp   Ser   Ile   Pro   Arg   Arg   Thr   Gly
145                           150                           155                         160

Ala   Glu   Val   Asp   Ile   Thr   Gly   Met   Thr   Met   Leu   Leu   Gln   Asn   Leu   Gly
                        165                           170                         175

Tyr   Ser   Val   Asp   Val   Lys   Lys   Asn   Leu   Thr   Ala   Ser   Asp   Met   Thr   Thr
                  180                           185                         190

Glu   Leu   Glu   Ala   Phe   Ala   His   Arg   Pro   Glu   His   Lys   Thr   Ser   Asp   Ser
            195                           200                         205

Thr   Phe   Leu   Val   Phe   Met   Ser   His   Gly   Ile   Arg   Glu   Gly   Ile   Cys   Gly
      210                           215                           220

Lys   Lys   His   Ser   Glu   Gln   Val   Pro   Asp   Ile   Leu   Gln   Leu   Asn   Ala   Ile
225                           230                           235                         240

Phe   Asn   Met   Leu   Asn   Thr   Lys   Asn   Cys   Pro   Ser   Leu   Lys   Asp   Lys   Pro
                        245                           250                         255

Lys   Val   Ile   Ile   Ile   Gln   Ala   Cys   Arg   Gly   Asp   Ser   Pro   Gly   Val   Val
                  260                           265                         270

Trp   Phe   Lys   Asp   Ser   Val   Gly   Val   Ser   Gly   Asn   Leu   Ser   Leu   Pro   Thr
            275                           280                         285

Thr   Glu   Glu   Phe   Glu   Asp   Asp   Ala   Ile   Lys   Lys   Ala   His   Ile   Glu   Lys
      290                           295                           300
```

| | | | | | | | | | | | | | | | | |
|---|---|---|---|---|---|---|---|---|---|---|---|---|---|---|---|---|
| Asp | Phe | Ile | Ala | Phe | Cys | Ser | Ser | Thr | Pro | Asp | Asn | Val | Ser | Trp | Arg | |
| 305 | | | | 310 | | | | | 315 | | | | | | 320 | |
| His | Pro | Thr | Met | Gly | Ser | Val | Phe | Ile | Gly | Arg | Leu | Ile | Glu | His | Met | |
| | | | | 325 | | | | | 330 | | | | | 335 | | |
| Gln | Glu | Tyr | Ala | Cys | Ser | Cys | Asp | Val | Glu | Ile | Phe | Arg | Lys | Val | | |
| | | | 340 | | | | | 345 | | | | 350 | | | | |
| Arg | Phe | Ser | Phe | Glu | Gln | Pro | Asp | Gly | Arg | Ala | Gln | Met | Pro | Thr | Thr | |
| | | 355 | | | | | 360 | | | | | 365 | | | | |
| Glu | Arg | Val | Thr | Leu | Thr | Arg | Cys | Phe | Tyr | Leu | Phe | Pro | Gly | His | | |
| | 370 | | | | | 375 | | | | | 380 | | | | | |

(2) INFORMATION FOR SEQ ID NO:5:

(i) SEQUENCE CHARACTERISTICS:
        (A) LENGTH: 969 base pairs
        (B) TYPE: nucleic acid
        (C) STRANDEDNESS: double
        (D) TOPOLOGY: linear (ii) MOLECULE TYPE: cDNA (ix) FEATURE:
        (A) NAME/KEY: CDS
        (B) LOCATION: 1..933

(xi) SEQUENCE DESCRIPTION: SEQ ID NO:5:

| | | | | | | | | | | | | | | | | |
|---|---|---|---|---|---|---|---|---|---|---|---|---|---|---|---|---|
| ATG | GCC | GAC | AAG | GTC | CTG | AAG | GAG | AAG | AGA | AAG | CTG | TTT | ATC | CGT | TCC | 48 |
| Met | Ala | Asp | Lys | Val | Leu | Lys | Glu | Lys | Arg | Lys | Leu | Phe | Ile | Arg | Ser | |
| 1 | | | | 5 | | | | | 10 | | | | | 15 | | |
| ATG | GGT | GAA | GCT | CCT | CAG | GCA | GTG | CAG | GAC | AAC | CCA | GCT | ATG | CCC | ACA | 96 |
| Met | Gly | Glu | Ala | Pro | Gln | Ala | Val | Gln | Asp | Asn | Pro | Ala | Met | Pro | Thr | |
| | | | 20 | | | | | 25 | | | | | 30 | | | |
| TCC | TCA | GGC | TCA | GAA | GGG | AAT | GTC | AAG | CTT | TGC | TCC | CTA | GAA | GAA | GCT | 144 |
| Ser | Ser | Gly | Ser | Glu | Gly | Asn | Val | Lys | Leu | Cys | Ser | Leu | Glu | Glu | Ala | |
| | | 35 | | | | | 40 | | | | | 45 | | | | |
| CAA | AGG | ATA | TGG | AAA | CAA | AAG | TCG | GCA | GAG | ATT | TAT | CCA | ATA | ATG | GAC | 192 |
| Gln | Arg | Ile | Trp | Lys | Gln | Lys | Ser | Ala | Glu | Ile | Tyr | Pro | Ile | Met | Asp | |
| | 50 | | | | | 55 | | | | | 60 | | | | | |
| AAG | TCA | AGC | CGC | ACA | CGT | CTT | GCT | CTC | ATT | ATC | TGC | AAT | GAA | GAA | TTT | 240 |
| Lys | Ser | Ser | Arg | Thr | Arg | Leu | Ala | Leu | Ile | Ile | Cys | Asn | Glu | Glu | Phe | |
| 65 | | | | | 70 | | | | | 75 | | | | | 80 | |
| GAC | AGT | ATT | CCT | AGA | AGA | ACT | GGA | GCT | GAG | GTT | GAC | ATC | ACA | GGC | ATG | 288 |
| Asp | Ser | Ile | Pro | Arg | Arg | Thr | Gly | Ala | Glu | Val | Asp | Ile | Thr | Gly | Met | |
| | | | | 85 | | | | | 90 | | | | | 95 | | |
| ACA | ATG | CTG | CTA | CAA | AAT | CTG | GGG | TAC | AGC | GTA | GAT | GTG | AAA | AAA | AAT | 336 |
| Thr | Met | Leu | Leu | Gln | Asn | Leu | Gly | Tyr | Ser | Val | Asp | Val | Lys | Lys | Asn | |
| | | | 100 | | | | | 105 | | | | | 110 | | | |
| CTC | ACT | GCT | TCG | GAC | ATG | ACT | ACA | GAG | CTG | GAG | GCA | TTT | GCA | CAC | CGC | 384 |
| Leu | Thr | Ala | Ser | Asp | Met | Thr | Thr | Glu | Leu | Glu | Ala | Phe | Ala | His | Arg | |
| | | 115 | | | | | 120 | | | | | 125 | | | | |
| CCA | GAG | CAC | AAG | ACC | TCT | GAC | AGC | ACG | TTC | CTG | GTG | TTC | ATG | TCT | CAT | 432 |
| Pro | Glu | His | Lys | Thr | Ser | Asp | Ser | Thr | Phe | Leu | Val | Phe | Met | Ser | His | |
| | 130 | | | | | 135 | | | | | 140 | | | | | |
| GGT | ATT | CGG | GAA | GGC | ATT | TGT | GGG | AAG | AAA | CAC | TCT | GAG | CAA | GTC | CCA | 480 |
| Gly | Ile | Arg | Glu | Gly | Ile | Cys | Gly | Lys | Lys | His | Ser | Glu | Gln | Val | Pro | |
| 145 | | | | | 150 | | | | | 155 | | | | | 160 | |
| GAT | ATA | CTA | CAA | CTC | AAT | GCA | ATC | TTT | AAC | ATG | TTG | AAT | ACC | AAG | AAC | 528 |
| Asp | Ile | Leu | Gln | Leu | Asn | Ala | Ile | Phe | Asn | Met | Leu | Asn | Thr | Lys | Asn | |
| | | | | 165 | | | | | 170 | | | | | 175 | | |
| TGC | CCA | AGT | TTG | AAG | GAC | AAA | CCG | AAG | GTG | ATC | ATC | ATC | CAG | GCC | TGC | 576 |
| Cys | Pro | Ser | Leu | Lys | Asp | Lys | Pro | Lys | Val | Ile | Ile | Ile | Gln | Ala | Cys | |
| | | | 180 | | | | | 185 | | | | | 190 | | | |

| | | | | | | | | | | | | | | | |
|---|---|---|---|---|---|---|---|---|---|---|---|---|---|---|---|
| CGT | GGT | GAC | AGC | CCT | GGT | GTG | GTG | TGG | TTT | AAA | GAT | TCA | GTA | GGA | GTT | 624
| Arg | Gly | Asp | Ser | Pro | Gly | Val | Val | Trp | Phe | Lys | Asp | Ser | Val | Gly | Val |
| | | 195 | | | | 200 | | | | | 205 | | | | |
| TCT | GGA | AAC | CTA | TCT | TTA | CCA | ACT | ACA | GAA | GAG | TTT | GAG | GAT | GAT | GCT | 672
| Ser | Gly | Asn | Leu | Ser | Leu | Pro | Thr | Thr | Glu | Glu | Phe | Glu | Asp | Asp | Ala |
| | 210 | | | | 215 | | | | | 220 | | | | | |
| ATT | AAG | AAA | GCC | CAC | ATA | GAG | AAG | GAT | TTT | ATC | GCT | TTC | TGC | TCT | TCC | 720
| Ile | Lys | Lys | Ala | His | Ile | Glu | Lys | Asp | Phe | Ile | Ala | Phe | Cys | Ser | Ser |
| 225 | | | | | 230 | | | | 235 | | | | | | 240 |
| ACA | CCA | GAT | AAT | GTT | TCT | TGG | AGA | CAT | CCC | ACA | ATG | GGC | TCT | GTT | TTT | 768
| Thr | Pro | Asp | Asn | Val | Ser | Trp | Arg | His | Pro | Thr | Met | Gly | Ser | Val | Phe |
| | | | | 245 | | | | | 250 | | | | | 255 | |
| ATT | GGA | AGA | CTC | ATT | GAA | CAT | ATG | CAA | GAA | TAT | GCC | TGT | TCC | TGT | GAT | 816
| Ile | Gly | Arg | Leu | Ile | Glu | His | Met | Gln | Glu | Tyr | Ala | Cys | Ser | Cys | Asp |
| | | | 260 | | | | | 265 | | | | | 270 | | |
| GTG | GAG | GAA | ATT | TTC | CGC | AAG | GTT | CGA | TTT | TCA | TTT | GAG | CAG | CCA | GAT | 864
| Val | Glu | Glu | Ile | Phe | Arg | Lys | Val | Arg | Phe | Ser | Phe | Glu | Gln | Pro | Asp |
| | | 275 | | | | | 280 | | | | | 285 | | | |
| GGT | AGA | GCG | CAG | ATG | CCC | ACC | ACT | GAA | AGA | GTG | ACT | TTG | ACA | AGA | TGT | 912
| Gly | Arg | Ala | Gln | Met | Pro | Thr | Thr | Glu | Arg | Val | Thr | Leu | Thr | Arg | Cys |
| | 290 | | | | | 295 | | | | | 300 | | | | |
| TTC | TAC | CTC | TTC | CCA | GGA | CAT | TAAAATAAGG | AAACTGTATG | AATGTCTGCG | | | | | | | 963
| Phe | Tyr | Leu | Phe | Pro | Gly | His | | | | | | | | | |
| 305 | | | | | 310 | | | | | | | | | | |
| GGCAGG | | | | | | | | | | | | | | | | 969

( 2 ) INFORMATION FOR SEQ ID NO:6:

( i ) SEQUENCE CHARACTERISTICS:
        ( A ) LENGTH: 311 amino acids
        ( B ) TYPE: amino acid
        ( D ) TOPOLOGY: linear ( i i ) MOLECULE TYPE: protein ( x i ) SEQUENCE DESCRIPTION: SEQ ID NO:6:

| | | | | | | | | | | | | | | |
|---|---|---|---|---|---|---|---|---|---|---|---|---|---|---|
| Met | Ala | Asp | Lys | Val | Leu | Lys | Glu | Lys | Arg | Lys | Leu | Phe | Ile | Arg | Ser |
| 1 | | | | 5 | | | | | 10 | | | | | 15 |
| Met | Gly | Glu | Ala | Pro | Gln | Ala | Val | Gln | Asp | Asn | Pro | Ala | Met | Pro | Thr |
| | | | 20 | | | | | 25 | | | | | 30 | | |
| Ser | Ser | Gly | Ser | Glu | Gly | Asn | Val | Lys | Leu | Cys | Ser | Leu | Glu | Glu | Ala |
| | | 35 | | | | | 40 | | | | | 45 | | | |
| Gln | Arg | Ile | Trp | Lys | Gln | Lys | Ser | Ala | Glu | Ile | Tyr | Pro | Ile | Met | Asp |
| | 50 | | | | | 55 | | | | | 60 | | | | |
| Lys | Ser | Ser | Arg | Thr | Arg | Leu | Ala | Leu | Ile | Ile | Cys | Asn | Glu | Glu | Phe |
| 65 | | | | | 70 | | | | | 75 | | | | | 80 |
| Asp | Ser | Ile | Pro | Arg | Arg | Thr | Gly | Ala | Glu | Val | Asp | Ile | Thr | Gly | Met |
| | | | | 85 | | | | | 90 | | | | | 95 | |
| Thr | Met | Leu | Leu | Gln | Asn | Leu | Gly | Tyr | Ser | Val | Asp | Val | Lys | Lys | Asn |
| | | | 100 | | | | | 105 | | | | | 110 | | |
| Leu | Thr | Ala | Ser | Asp | Met | Thr | Thr | Glu | Leu | Glu | Ala | Phe | Ala | His | Arg |
| | | | 115 | | | | 120 | | | | | 125 | | | |
| Pro | Glu | His | Lys | Thr | Ser | Asp | Ser | Thr | Phe | Leu | Val | Phe | Met | Ser | His |
| | | 130 | | | | | 135 | | | | | 140 | | | |
| Gly | Ile | Arg | Glu | Gly | Ile | Cys | Gly | Lys | Lys | His | Ser | Glu | Gln | Val | Pro |
| 145 | | | | | 150 | | | | | 155 | | | | | 160 |
| Asp | Ile | Leu | Gln | Leu | Asn | Ala | Ile | Phe | Asn | Met | Leu | Asn | Thr | Lys | Asn |
| | | | | 165 | | | | | 170 | | | | | 175 | |
| Cys | Pro | Ser | Leu | Lys | Asp | Lys | Pro | Lys | Val | Ile | Ile | Ile | Gln | Ala | Cys |

```
                        180                           185                           190
Arg  Gly  Asp  Ser  Pro  Gly  Val  Val  Trp  Phe  Lys  Asp  Ser  Val  Gly  Val
               195                      200                     205

Ser  Gly  Asn  Leu  Ser  Leu  Pro  Thr  Thr  Glu  Glu  Phe  Glu  Asp  Asp  Ala
     210                      215                     220

Ile  Lys  Lys  Ala  His  Ile  Glu  Lys  Asp  Phe  Ile  Ala  Phe  Cys  Ser  Ser
225                      230                     235                          240

Thr  Pro  Asp  Asn  Val  Ser  Trp  Arg  His  Pro  Thr  Met  Gly  Ser  Val  Phe
                    245                     250                          255

Ile  Gly  Arg  Leu  Ile  Glu  His  Met  Gln  Glu  Tyr  Ala  Cys  Ser  Cys  Asp
               260                      265                     270

Val  Glu  Glu  Ile  Phe  Arg  Lys  Val  Arg  Phe  Ser  Phe  Glu  Gln  Pro  Asp
          275                      280                     285

Gly  Arg  Ala  Gln  Met  Pro  Thr  Thr  Glu  Arg  Val  Thr  Leu  Thr  Arg  Cys
     290                      295                     300

Phe  Tyr  Leu  Phe  Pro  Gly  His
305                      310
```

( 2 ) INFORMATION FOR SEQ ID NO:7:

( i ) SEQUENCE CHARACTERISTICS:
        ( A ) LENGTH: 825 base pairs
        ( B ) TYPE: nucleic acid
        ( C ) STRANDEDNESS: double
        ( D ) TOPOLOGY: linear ( i i ) MOLECULE TYPE: cDNA ( i x ) FEATURE:
        ( A ) NAME/KEY: CDS
        ( B ) LOCATION: 1..789

( x i ) SEQUENCE DESCRIPTION: SEQ ID NO:7:

```
ATG  GCC  GAC  AAG  GTC  CTG  AAG  GAG  AAG  AGA  AAG  CTG  TTT  ATC  CGT  TCC     48
Met  Ala  Asp  Lys  Val  Leu  Lys  Glu  Lys  Arg  Lys  Leu  Phe  Ile  Arg  Ser
 1                   5                        10                      15

ATG  GGT  GAA  GCT  CCT  CAG  GCA  GTG  CAG  GAC  AAC  CCA  GCT  ATG  CCC  ACA     96
Met  Gly  Glu  Ala  Pro  Gln  Ala  Val  Gln  Asp  Asn  Pro  Ala  Met  Pro  Thr
               20                        25                           30

TCC  TCA  GGC  TCA  GAA  GGG  AAT  GTC  AAG  CTT  TGC  TCC  CTA  GAA  GAA  GCT    144
Ser  Ser  Gly  Ser  Glu  Gly  Asn  Val  Lys  Leu  Cys  Ser  Leu  Glu  Glu  Ala
               35                        40                      45

CAA  AGG  ATA  TGG  AAA  CAA  AAG  TCG  GCA  GAG  ATT  TAT  CCA  ATA  ATG  GAC    192
Gln  Arg  Ile  Trp  Lys  Gln  Lys  Ser  Ala  Glu  Ile  Tyr  Pro  Ile  Met  Asp
      50                        55                           60

AAG  TCA  AGC  CGC  ACA  CGT  CTT  GCT  CTC  ATT  ATC  TGC  AAT  GAA  GAA  TTT    240
Lys  Ser  Ser  Arg  Thr  Arg  Leu  Ala  Leu  Ile  Ile  Cys  Asn  Glu  Glu  Phe
 65                       70                         75                      80

GAC  AGT  ATT  CCT  AGA  AGA  ACT  GGA  GCT  GAG  GTT  GAC  ATC  ACA  GGC  ATG    288
Asp  Ser  Ile  Pro  Arg  Arg  Thr  Gly  Ala  Glu  Val  Asp  Ile  Thr  Gly  Met
                    85                        90                          95

ACA  ATG  CTG  CTA  CAA  AAT  CTG  GGG  TAC  AGC  GTA  GAT  GTG  AAA  AAA  AAT    336
Thr  Met  Leu  Leu  Gln  Asn  Leu  Gly  Tyr  Ser  Val  Asp  Val  Lys  Lys  Asn
               100                      105                     110

CTC  ACT  GCT  TCG  GAC  ATG  ACT  ACA  GAG  CTG  GAG  GCA  TTT  GCA  CAC  CGC    384
Leu  Thr  Ala  Ser  Asp  Met  Thr  Thr  Glu  Leu  Glu  Ala  Phe  Ala  His  Arg
               115                      120                     125

CCA  GAG  CAC  AAG  ACC  TCT  GAC  AGC  ACG  TTC  CTG  GTG  TTC  ATG  TCT  CAT    432
Pro  Glu  His  Lys  Thr  Ser  Asp  Ser  Thr  Phe  Leu  Val  Phe  Met  Ser  His
     130                      135                          140

GGT  ATT  CGG  GAA  GGC  ATT  TGT  GGG  AAG  AAA  CAC  TCT  GAG  CAA  GTC  CCA    480
```

```
Gly Ile Arg Glu Gly Ile Cys Gly Lys Lys His Ser Glu Gln Val Pro
145                 150                 155                 160

GAT ATA CTA CAA CTC AAT GCA ATC TTT AAC ATG TTG AAT ACC AAG AAC    528
Asp Ile Leu Gln Leu Asn Ala Ile Phe Asn Met Leu Asn Thr Lys Asn
                165                 170                 175

TGC CCA AGT TTG AAG GAC AAA CCG AAG GTG ATC ATC ATC CAG GCC TGC    576
Cys Pro Ser Leu Lys Asp Lys Pro Lys Val Ile Ile Ile Gln Ala Cys
            180                 185                 190

CGT GGT GAT AAT GTT TCT TGG AGA CAT CCC ACA ATG GGC TCT GTT TTT    624
Arg Gly Asp Asn Val Ser Trp Arg His Pro Thr Met Gly Ser Val Phe
        195                 200                 205

ATT GGA AGA CTC ATT GAA CAT ATG CAA GAA TAT GCC TGT TCC TGT GAT    672
Ile Gly Arg Leu Ile Glu His Met Gln Glu Tyr Ala Cys Ser Cys Asp
    210                 215                 220

GTG GAG GAA ATT TTC CGC AAG GTT CGA TTT TCA TTT GAG CAG CCA GAT    720
Val Glu Glu Ile Phe Arg Lys Val Arg Phe Ser Phe Glu Gln Pro Asp
225                 230                 235                 240

GGT AGA GCG CAG ATG CCC ACC ACT GAA AGA GTG ACT TTG ACA AGA TGT    768
Gly Arg Ala Gln Met Pro Thr Thr Glu Arg Val Thr Leu Thr Arg Cys
                245                 250                 255

TTC TAC CTC TTC CCA GGA CAT TAAAATAAGG AAACTGTATG AATGTCTGCG        819
Phe Tyr Leu Phe Pro Gly His
            260

GGCAGG                                                              825
```

( 2 ) INFORMATION FOR SEQ ID NO:8:

( i ) SEQUENCE CHARACTERISTICS:
        ( A ) LENGTH: 263 amino acids
        ( B ) TYPE: amino acid
        ( D ) TOPOLOGY: linear ( i i ) MOLECULE TYPE: protein ( x i ) SEQUENCE DESCRIPTION: SEQ ID NO:8:

```
Met Ala Asp Lys Val Leu Lys Glu Lys Arg Lys Leu Phe Ile Arg Ser
1               5                   10                  15

Met Gly Glu Ala Pro Gln Ala Val Gln Asp Asn Pro Ala Met Pro Thr
            20                  25                  30

Ser Ser Gly Ser Glu Gly Asn Val Lys Leu Cys Ser Leu Glu Glu Ala
        35                  40                  45

Gln Arg Ile Trp Lys Gln Lys Ser Ala Glu Ile Tyr Pro Ile Met Asp
    50                  55                  60

Lys Ser Ser Arg Thr Arg Leu Ala Leu Ile Ile Cys Asn Glu Glu Phe
65                  70                  75                  80

Asp Ser Ile Pro Arg Arg Thr Gly Ala Glu Val Asp Ile Thr Gly Met
                85                  90                  95

Thr Met Leu Leu Gln Asn Leu Gly Tyr Ser Val Asp Val Lys Lys Asn
            100                 105                 110

Leu Thr Ala Ser Asp Met Thr Thr Glu Leu Glu Ala Phe Ala His Arg
        115                 120                 125

Pro Glu His Lys Thr Ser Asp Ser Thr Phe Leu Val Phe Met Ser His
    130                 135                 140

Gly Ile Arg Glu Gly Ile Cys Gly Lys Lys His Ser Glu Gln Val Pro
145                 150                 155                 160

Asp Ile Leu Gln Leu Asn Ala Ile Phe Asn Met Leu Asn Thr Lys Asn
                165                 170                 175

Cys Pro Ser Leu Lys Asp Lys Pro Lys Val Ile Ile Ile Gln Ala Cys
            180                 185                 190
```

```
Arg  Gly  Asp  Asn  Val  Ser  Trp  Arg  His  Pro  Thr  Met  Gly  Ser  Val  Phe
          195                      200                      205

Ile  Gly  Arg  Leu  Ile  Glu  His  Met  Gln  Glu  Tyr  Ala  Cys  Ser  Cys  Asp
          210                      215                      220

Val  Glu  Glu  Ile  Phe  Arg  Lys  Val  Arg  Phe  Ser  Phe  Glu  Gln  Pro  Asp
225                      230                      235                      240

Gly  Arg  Ala  Gln  Met  Pro  Thr  Thr  Glu  Arg  Val  Thr  Leu  Thr  Arg  Cys
                    245                      250                      255

Phe  Tyr  Leu  Phe  Pro  Gly  His
                    260
```

( 2 ) INFORMATION FOR SEQ ID NO:9:

( i ) SEQUENCE CHARACTERISTICS:
        ( A ) LENGTH: 300 base pairs
        ( B ) TYPE: nucleic acid
        ( C ) STRANDEDNESS: double
        ( D ) TOPOLOGY: linear ( i i ) MOLECULE TYPE: cDNA ( i x ) FEATURE:
        ( A ) NAME/KEY: CDS
        ( B ) LOCATION: 1..264

( x i ) SEQUENCE DESCRIPTION: SEQ ID NO:9:

```
ATG  GCC  GAC  AAG  GTC  CTG  AAG  GAG  AAG  AGA  AAG  CTG  TTT  ATC  CGT  TCC       48
Met  Ala  Asp  Lys  Val  Leu  Lys  Glu  Lys  Arg  Lys  Leu  Phe  Ile  Arg  Ser
 1                   5                        10                       15

ATG  GGT  GAA  GAT  AAT  GTT  TCT  TGG  AGA  CAT  CCC  ACA  ATG  GGC  TCT  GTT       96
Met  Gly  Glu  Asp  Asn  Val  Ser  Trp  Arg  His  Pro  Thr  Met  Gly  Ser  Val
               20                        25                       30

TTT  ATT  GGA  AGA  CTC  ATT  GAA  CAT  ATG  CAA  GAA  TAT  GCC  TGT  TCC  TGT      144
Phe  Ile  Gly  Arg  Leu  Ile  Glu  His  Met  Gln  Glu  Tyr  Ala  Cys  Ser  Cys
               35                        40                       45

GAT  GTG  GAG  GAA  ATT  TTC  CGC  AAG  GTT  CGA  TTT  TCA  TTT  GAG  CAG  CCA      192
Asp  Val  Glu  Glu  Ile  Phe  Arg  Lys  Val  Arg  Phe  Ser  Phe  Glu  Gln  Pro
     50                        55                       60

GAT  GGT  AGA  GCG  CAG  ATG  CCC  ACC  ACT  GAA  AGA  GTG  ACT  TTG  ACA  AGA      240
Asp  Gly  Arg  Ala  Gln  Met  Pro  Thr  Thr  Glu  Arg  Val  Thr  Leu  Thr  Arg
 65                       70                        75                       80

TGT  TTC  TAC  CTC  TTC  CCA  GGA  CAT  TAAAATAAGG  AAACTGTATG  AATGTCTGCG          294
Cys  Phe  Tyr  Leu  Phe  Pro  Gly  His
                    85

GGCAGG                                                                               300
```

( 2 ) INFORMATION FOR SEQ ID NO:10:

( i ) SEQUENCE CHARACTERISTICS:
        ( A ) LENGTH: 88 amino acids
        ( B ) TYPE: amino acid
        ( D ) TOPOLOGY: linear ( i i ) MOLECULE TYPE: protein ( x i ) SEQUENCE DESCRIPTION: SEQ ID NO:10:

```
Met  Ala  Asp  Lys  Val  Leu  Lys  Glu  Lys  Arg  Lys  Leu  Phe  Ile  Arg  Ser
 1                   5                        10                       15

Met  Gly  Glu  Asp  Asn  Val  Ser  Trp  Arg  His  Pro  Thr  Met  Gly  Ser  Val
               20                        25                       30

Phe  Ile  Gly  Arg  Leu  Ile  Glu  His  Met  Gln  Glu  Tyr  Ala  Cys  Ser  Cys
               35                        40                       45
```

| Asp | Val | Glu | Glu | Ile | Phe | Arg | Lys | Val | Arg | Phe | Ser | Phe | Glu | Gln | Pro |
|---|---|---|---|---|---|---|---|---|---|---|---|---|---|---|---|
| | 50 | | | | | 55 | | | | | 60 | | | | |

| Asp | Gly | Arg | Ala | Gln | Met | Pro | Thr | Thr | Glu | Arg | Val | Thr | Leu | Thr | Arg |
|---|---|---|---|---|---|---|---|---|---|---|---|---|---|---|---|
| 65 | | | | | 70 | | | | 75 | | | | | | 80 |

| Cys | Phe | Tyr | Leu | Phe | Pro | Gly | His |
|---|---|---|---|---|---|---|---|
| | | | | 85 | | | |

(2) INFORMATION FOR SEQ ID NO:11:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:11:

CAGAACGATC TCTTCAC                                                17

(2) INFORMATION FOR SEQ ID NO:12:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:12:

ATGGCCGACA AGGTCCTG                                            18

(2) INFORMATION FOR SEQ ID NO:13:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:13:

CCTGCCCGCA GACATTCA                                            18

(2) INFORMATION FOR SEQ ID NO:14:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:14:

GGTTTCCAGA AACTCCTACT TAATC                                  25

(2) INFORMATION FOR SEQ ID NO:15:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA ( x i ) SEQUENCE DESCRIPTION: SEQ ID NO:15:

ATGGCTATTA AGAAAGCCCA CATA 24

( 2 ) INFORMATION FOR SEQ ID NO:16:

( i ) SEQUENCE CHARACTERISTICS:
    ( A ) LENGTH: 30 base pairs
    ( B ) TYPE: nucleic acid
    ( C ) STRANDEDNESS: single
    ( D ) TOPOLOGY: linear ( i i ) MOLECULE TYPE: cDNA ( x i ) SEQUENCE DESCRIPTION: SEQ ID NO:16:

GGGATCCTGA ACCCAGCTAT GCCCACATCC 30

( 2 ) INFORMATION FOR SEQ ID NO:17:

( i ) SEQUENCE CHARACTERISTICS:
    ( A ) LENGTH: 29 base pairs
    ( B ) TYPE: nucleic acid
    ( C ) STRANDEDNESS: double
    ( D ) TOPOLOGY: linear ( i i ) MOLECULE TYPE: cDNA ( x i ) SEQUENCE DESCRIPTION: SEQ ID NO:17:

GCAGGTAAGG GTCATCTCTT GCAGCTCCT 29

( 2 ) INFORMATION FOR SEQ ID NO:18:

( i ) SEQUENCE CHARACTERISTICS:
    ( A ) LENGTH: 29 base pairs
    ( B ) TYPE: nucleic acid
    ( C ) STRANDEDNESS: double
    ( D ) TOPOLOGY: linear ( i i ) MOLECULE TYPE: cDNA ( x i ) SEQUENCE DESCRIPTION: SEQ ID NO:18:

GAAGGTACAA TAAATCTCTT GCAGCTCCT 29

( 2 ) INFORMATION FOR SEQ ID NO:19:

( i ) SEQUENCE CHARACTERISTICS:
    ( A ) LENGTH: 29 base pairs
    ( B ) TYPE: nucleic acid
    ( C ) STRANDEDNESS: double
    ( D ) TOPOLOGY: linear ( i i ) MOLECULE TYPE: cDNA ( x i ) SEQUENCE DESCRIPTION: SEQ ID NO:19:

GAAGGTACAA TAAATCTCTT GCAGCTCCT 29

( 2 ) INFORMATION FOR SEQ ID NO:20:

( i ) SEQUENCE CHARACTERISTICS:
    ( A ) LENGTH: 29 base pairs
    ( B ) TYPE: nucleic acid
    ( C ) STRANDEDNESS: double
    ( D ) TOPOLOGY: linear ( i i ) MOLECULE TYPE: cDNA ( x i ) SEQUENCE DESCRIPTION: SEQ ID NO:20:

GGTGGTGAGT GCTGTTATCC ATAGATAAT 29

( 2 ) INFORMATION FOR SEQ ID NO:21:

( i ) SEQUENCE CHARACTERISTICS:
        ( A ) LENGTH: 29 base pairs
        ( B ) TYPE: nucleic acid
        ( C ) STRANDEDNESS: double
        ( D ) TOPOLOGY: linear ( i i ) MOLECULE TYPE: cDNA ( x i ) SEQUENCE DESCRIPTION: SEQ ID NO:21:

GAAGGTACAA TAAATTATCC ATAGATAAT    29

( 2 ) INFORMATION FOR SEQ ID NO:22:

( i ) SEQUENCE CHARACTERISTICS:
        ( A ) LENGTH: 9 base pairs
        ( B ) TYPE: nucleic acid
        ( C ) STRANDEDNESS: double
        ( D ) TOPOLOGY: linear ( i i ) MOLECULE TYPE: cDNA ( x i ) SEQUENCE DESCRIPTION: SEQ ID NO:22:

GCAGCTCCT    9

( 2 ) INFORMATION FOR SEQ ID NO:23:

( i ) SEQUENCE CHARACTERISTICS:
        ( A ) LENGTH: 19 base pairs
        ( B ) TYPE: nucleic acid
        ( C ) STRANDEDNESS: double
        ( D ) TOPOLOGY: linear ( i i ) MOLECULE TYPE: cDNA ( x i ) SEQUENCE DESCRIPTION: SEQ ID NO:23:

GAAGGTACAA TAAACTCCT    19

( 2 ) INFORMATION FOR SEQ ID NO:24:

( i ) SEQUENCE CHARACTERISTICS:
        ( A ) LENGTH: 9 base pairs
        ( B ) TYPE: nucleic acid
        ( C ) STRANDEDNESS: double
        ( D ) TOPOLOGY: linear ( i i ) MOLECULE TYPE: cDNA ( x i ) SEQUENCE DESCRIPTION: SEQ ID NO:24:

GGTGATAAT    9

( 2 ) INFORMATION FOR SEQ ID NO:25:

( i ) SEQUENCE CHARACTERISTICS:
        ( A ) LENGTH: 19 base pairs
        ( B ) TYPE: nucleic acid
        ( C ) STRANDEDNESS: double
        ( D ) TOPOLOGY: linear ( i i ) MOLECULE TYPE: cDNA ( x i ) SEQUENCE DESCRIPTION: SEQ ID NO:25:

GAAGGTACAA TAAAATAAT    19

ISOFORMS OF HUMAN INTERLEUKIN-1β CONVERTING ENZYME AND METHODS OF USING THE SAME

ACKNOWLEDGEMENT OF GOVERNMENT RIGHTS

This invention was made with Government support under Grant AI 35035-01 from the National Institutes of Health. The Government has certain rights in this invention.

FIELD OF THE INVENTION

The invention relates to the identification and cloning of four alternatively spliced mRNA that encode four isoforms of human interleukin-1β converting enzyme (ICE) with different apoptotic activities and to methods of making and using the same.

BACKGROUND OF THE INVENTION

Interleukin-1β converting enzyme, which is referred to herein as ICEα, is a cytoplasmic cysteine protease that cleaves inactive 31 kDa proIL-1β to generate the active 17.5 kDa proinflammatory cytokine IL-1β (Black, R. A., et al. (1989) FEBS Lett. 247, 386–390; and Kostura, M. J., et al. (1989) Proc. Natl. Acad. Sci. USA 86, 5227–5231, which are each incorporated herein by reference). ICEα is expressed in many tissues as an inactive proenzyme polypeptide of 404 amino acids (SEQ ID NO:2) and a relative molecular mass (Mr) of 45 kDa (p45) (Cerretti, D. P., et al. (1992) Science 256, 97–100; and Thornberry, N. A., et al. (1992) Nature 356, 768–774).

Active ICEα is produced after proteolytic cleavage of the proenzyme p45 to generate two subunits of Mr 20 kDa and 10 kDa, known as p20 and p10 subunits. Recent crystal structure analysis of active ICES demonstrated that the two subunits associate with each other to form a $(p20)_2/(p10)_2$ tetramer (Wilson, K. P., et al. (1994) Nature 370, 270–275) also referred to as a $(p20/p10)_2$ homodimer (Walker, N. P. C., et al. (1994) Cell 78, 343–352).

The structure of ICEα is unique and is not related to any known protein structures including those of other cysteine proteases. ICEα is also unusual in its substrate specificity. ICEα requires an Asp in the P1 position and a small preferably hydrophobic residue in the P1' position (Sleath, P. R., et al. (1990) J. Biol. Chem. 265, 14526–14528; and Howard, A. D., et al. (1991) J. Immunol. 147, 2964–2969). Only the serine protease granzyme B and its homologs have a similar requirement for Asp in the P1 position.

Sequence homology between ICEα and the *Caenorhabditis elegans* cell death gene product CED-3 suggests that mammalian ICEα or its homologs might be involved in apoptosis. The two proteins share an overall 28% sequence identity (Yuan, J., et al. (1993) Cell 75, 641–652). A 43% identity is observed when a region which contains the enzyme active site is compared. A significant homology between ICEα or CED-3, and a newly discovered mouse protein known as Nedd2 was also demonstrated in a recent study and the significance of this homology to CED-3 was demonstrated when overexpression of ICES or Nedd2 in fibroblasts resulted in apoptosis (Kumar, S., et al. (1994) Genes & Develpoment 8, 1613–1626; and Miura, M., et al. (1993) Cell 75, 653–660). Expression of crmA, a poxvirus specific inhibitor of ICEα (Ray, C., et al. (1992) Cell 69, 597–604) was able to block ICEα apoptosis in fibroblasts and to protect ganglion neurons from apoptosis induced by nerve growth factor depletion (Gagliardini, V., et al. (1994) Science 263, 826–828).

There is a need for compounds which inhibit activity of ICE isoforms. There is a need for kits and methods of identifying such compounds. There is a need for isolated ICE isoforms, and for compositions and methods of producing and isolating ICE isoforms.

SUMMARY OF THE INVENTION

The present invention relates to substantially pure interleukin-1 converting enzyme isoforms.

The present invention relates to substantially pure interleukin-1 converting enzyme isoforms having the amino acid sequence of SEQ ID NO:4, SEQ ID NO:6, SEQ ID NO:8 or SEQ ID NO:10.

The present invention relates to pharmaceutical compositions comprising one or more of the interleukin-1 converting enzyme isoforms.

The present invention relates to nucleic acid molecules that encode interleukin-1 converting enzyme isoforms.

The present invention relates to nucleic acid molecules encoding interleukin-1 converting enzyme isoforms that consist of SEQ ID NO:3, SEQ ID NO:5, SEQ ID NO:7 or SEQ ID NO:9.

The present invention relates to recombinant expression vectors that comprise a nucleic acid sequence that encodes an interleukin-1 converting enzyme isoform.

The present invention relates to host cells that comprise recombinant expression vectors that encode interleukin-1 converting enzyme isoforms.

The present invention relates to fragments of nucleic acid molecules with sequences encoding interleukin-1 converting enzyme isoform that have at least 10 nucleotides.

The present invention relates to oligonucleotide molecules that comprise a nucleotide sequence complimentary to a nucleotide sequence of at least 10 nucleotides of SEQ ID NO:3, SEQ ID NO:5, SEQ ID NO:7 or SEQ ID NO:9.

The present invention relates to isolated antibodies which bind to an epitope on SEQ ID NO:4, SEQ ID NO:6, SEQ ID NO:8 or SEQ ID NO:10.

The present invention relates to methods of identifying inhibitors of ICE isoforms. The methods comprise performing a control assay by contacting an ICE isoform with proIL-1β in the absence of a test compound under conditions in which the ICE isoform processes the proIL-1β, then performing a test assay by contacting an ICE isoform with proIL-1β in the presence of a test compound under conditions in which said ICE isoform processes the proIL-1β in the absence of said test compound, and then comparing the results of the two assays and determining whether the ICE isoform is active in the absence of test compound in the control assay and processes the proIL-1β but is not active in the presence of test compound in the test assay and does not processes the proIL-1β.

DETAILED DESCRIPTION OF THE INVENTION

The present invention provides four novel human ICE mRNA isoforms which have been identified and characterized. The four isoforms of the ICE protein encoded by these mRNAs are designated ICEα, ICEγ, ICEδ and ICEε. Together with ICEα, the four isoforms make up a family of five proteins in which three members, ICEα, ICEβ, and ICEγ, have similar function; ICEδ and ICEε function as inhibitors.

The discovery of the four distinct isoforms provides the means to design and discover isoform specific inhibitors.

According to the present invention, two of the four isoforms, ICEβ and ICEγ have a similar function as ICEα. These ICE isoforms may be used to screen compounds for isoform specific inhibitors. Inhibitors are useful as anti-inflammatory and anti-apoptotic agents. Kits are provided for screening compounds for ICE specific inhibitors. The nucleotide sequences of the isoforms disclosed herein allows for the production of pure proteins and the design of probes which specifically hybridize to nucleic acid molecules that encode ICE isoforms and antisense compounds to inhibit transcription of specific isoforms of ICE. Anti-ICE antibodies are provided which are specific for each of ICEβ, ICEγ and ICEδ as well as ICEε. Such antibodies are isoform specific inhibitors of ICE and may be used in methods of isolating pure ICE isoforms and methods of inhibiting ICE isoform activity. ICEε has been discovered to be an effective ICE inhibitor. According to this aspect of the invention, ICEε may be provided as a composition for inhibiting ICE in methods of inhibiting ICE.

The four cDNAs that encode the isoforms ICEβ, ICEγ, ICEδ and ICEε result from one or more alternative splicing events involving exons 2 to 7 of the ICE gene (Cerretti, D. P., et al. (1994) *Genomics* 20, 468–473). In ICEβ the deletion of exon 3 resulted from splicing of the DNA sequence between exon 2 and 4 using intron 2 splice donor and intron 3 splice acceptor (Tables I and II). Similarly, the deletion of exon 7 in ICEδ resulted from splicing of the DNA sequence between exon 6 and 8 using intron 6 splice donor and intron 7 splice acceptor (Tables I and II). On the other hand, the deletions within exon 2 to 7 in ICEγ, δ and ε resulted from the use of an alternative splice donor located within the coding sequence of exon 2 (Tables I and II). However, in ICEγ and δ intron 3 splice acceptor was used whereas in ICEε intron 7 splice acceptor was used (Tables I and II).

Three ICE mRNA species (2.5 kb, 1.9 kb and 0.5 kb) have been detected in THP-1 cell line and several other normal human tissues including peripheral blood monocytes, peripheral blood lymphocytes, peripheral blood neutrophils, resting and activated peripheral blood T-lymphocytes and placenta (Cerretti, D. P., et al. (1992) *Science* 256, 97–100). The smallest 0.5 kb mRNA may be the ICEε isoform which is highly expressed in peripheral blood neutrophils and placenta.

The present invention provides substantially purified ICE isoforms ICEβ, ICEγ, ICEδ and ICEε which have amino acid sequences consisting of: SEQ ID NO:4, SEQ ID NO:6, SEQ ID NO:8 and SEQ ID NO:10, respectively. ICE isoforms ICEβ, ICEγ, ICEδ and ICEε can be isolated from natural sources, produced by recombinant DNA methods or synthesized by standard protein synthesis techniques.

Antibodies which specifically bind to a particular ICE isoform may be used to purify the protein from natural sources using well known techniques and readily available starting materials. Such antibodies may also be used to purify the ICE isoform from material present when producing the protein by recombinant DNA methodology. The present invention relates to antibodies that bind to an epitope which is present on an ICE isoform selected from the group consisting of: ICEβ—SEQ ID NO:4, ICEγ—SEQ ID NO:6, ICEδ—SEQ ID NO:8, and ICEε—SEQ ID NO:10. As used herein, the term "antibody" is meant to refer to complete, intact antibodies, and Fab fragments and F(ab)₂ fragments thereof. Complete, intact antibodies include monoclonal antibodies such as murine monoclonal antibodies, chimeric antibodies and humanized antibodies. In some embodiments, the antibodies specifically bind to an epitope of only one of: ICEβ—SEQ ID NO:4, ICEγ—SEQ ID NO:6, ICEδ—SEQ ID NO:8, and ICEε—SEQ ID NO:10. Antibodies that bind to an epitope which is present on an ICE isoform are useful to isolate and purify the ICE isoform from both natural sources or recombinant expression systems using well known techniques such as affinity chromatography. Such antibodies are useful to detect the presence of such protein in a sample and to determine if cells are expressing the protein.

The production of antibodies and the protein structures of complete, intact antibodies, Fab fragments and F(ab)₂ fragments and the organization of the genetic sequences that encode such molecules are well known and are described, for example, in Harlow, E. and D. Lane (1988) *ANTIBODIES: A Laboratory Manual*, Cold Spring Harbor Laboratory, Cold Spring Harbor, N.Y. which is incorporated herein by reference. Briefly, for example, the ICE isoform protein, or an immunogenic fragment thereof is injected into mice. The spleen of the mouse is removed, the spleen cells are isolated and fused with immortalized mouse cells. The hybrid cells, or hybridomas, are cultured and those cells which secrete antibodies are selected. The antibodies are analyzed and, if found to specifically bind to the ICE isoform, the hybridoma which produces them is cultured to produce a continuous supply of antibodies.

Using standard techniques and readily available starting materials, a nucleic acid molecule that encodes each of the ICE isoform may be isolated from a cDNA library, using probes which are designed using the nucleotide sequence information disclosed in SEQ ID NO:3, SEQ ID NO:5, SEQ ID NO:7, or SEQ ID NO:9. The present invention relates to an isolated nucleic acid molecule that comprises a nucleotide sequence that encodes an ICE isoform selected from the group consisting of ICEβ, ICEγ, ICEδ, and ICEε that comprises the amino acid sequence of SEQ ID NO:4, SEQ ID NO:6, SEQ ID NO:8 and SEQ ID NO:10, respectively. In some embodiments, the nucleic acid molecules consist of a nucleotide sequence that encodes ICEβ, ICEγ, ICEδ or ICEε. In some embodiments, the nucleic acid molecules comprise the nucleotide sequence that consists of the coding sequence in SEQ ID NO:3, SEQ ID NO:5, SEQ ID NO:7 or SEQ ID NO:9. In some embodiments, the nucleic acid molecules consist of the nucleotide sequence set forth in SEQ ID NO:3, SEQ ID NO:5, SEQ ID NO:7 and SEQ ID NO:9. The isolated nucleic acid molecules of the invention are useful to prepare constructs and recombinant expression systems for preparing the ICE isoforms of the invention.

A cDNA library may be generated by well known techniques. A cDNA clone which contains one of the nucleotide sequences set out is identified using probes that comprise at least a portion of the nucleotide sequence disclosed in SEQ ID NO:3, SEQ ID NO:5, SEQ ID NO:7 or SEQ ID NO:9. The probes have at least 16 nucleotides, preferably 24 nucleotides. The probes are used to screen the cDNA library using standard hybridization techniques. Alternatively, genomic clones may be isolated using genomic DNA from any human cell as a starting material. The present invention relates to isolated nucleic acid molecules that comprise a nucleotide sequence identical or complementary to a fragment of SEQ ID NO:3, SEQ ID NO:5, SEQ ID NO:7 or SEQ ID NO:9 which is at least 10 nucleotides. In some embodiments, the isolated nucleic acid molecules consist of a nucleotide sequence identical or complementary to a fragment of SEQ ID NO:3, SEQ ID NO:5, SEQ ID NO:7 or SEQ ID NO:9 which is at least 10 nucleotides. In some embodiments, the isolated nucleic acid molecules comprise or consist of a nucleotide sequence identical or complementary to a fragment of SEQ ID NO:3, SEQ ID NO:5, SEQ ID NO:7 or SEQ ID NO:9 which is 15–150 nucleotides. In some embodiments, the isolated nucleic acid molecules comprise or consist of a nucleotide sequence identical or complementary to a fragment of SEQ ID NO:3, SEQ ID NO:5, SEQ ID NO:7 or SEQ ID NO:9 which is 15–30 nucleotides. Isolated nucleic acid molecules that comprise or consist of a nucleotide sequence identical or complementary to a fragment of SEQ ID NO:3, SEQ ID NO:5, SEQ ID NO:7 or SEQ ID NO:9 which is at least 10 nucleotides are useful as probes for identifying genes and cDNA sequence having SEQ ID NO:3, SEQ ID NO:5, SEQ ID NO:7 or SEQ ID NO:9, respectively, PCR primers for amplifying genes and cDNA having SEQ ID NO:3, SEQ ID NO:5, SEQ ID NO:7 or SEQ ID NO:9, respectively, and antisense molecules for inhibiting transcription and translation of genes and cDNA, respectively, which encode ICE isoforms having the amino acid sequence of SEQ ID NO:4, SEQ ID NO:6, SEQ ID NO:8 or SEQ ID NO:10, respectively.

The cDNA that encodes an ICE isoform may be used as a molecular marker in electrophoresis assays in which cDNA from a sample is separated on an electrophoresis gel and ICE isoform probes are used to identify bands which hybridize to such probes. Specifically, SEQ ID NO:3 or portions thereof, SEQ ID NO:5 or portions thereof, SEQ ID NO:7 or portions thereof and SEQ ID NO:9 or portions thereof, may be used as a molecular marker in electrophoresis assays in which cDNA from a sample is separated on an electrophoresis gel and ICE isoform specific probes are used to identify bands which hybridize to them, indicating that the band has a nucleotide sequence complementary to the sequence of the probes. The isolated nucleic acid molecule provided as a size marker will show up as a positive band which is known to hybridize to the probes and thus can be used as a reference point to the size of cDNA that encodes ICEβ, ICEγ, ICEδ and ICEε, respectively. Electrophoresis gels useful in such an assay include standard polyacrylamide gels as described in Sambrook et al., *Molecular Cloning a Laboratory Manual,* Second Ed. Cold Spring Harbor Press (1989) which is incorporated herein by reference.

The nucleotide sequence in SEQ ID NO:3, SEQ ID NO:5, SEQ ID NO:7 and SEQ ID NO:9, may be used to design probes, primers and complimentary molecules which specifically hybridize to the unique nucleotide sequences of ICEβ, ICEγ, ICEδ and ICEε, respectively. Probes, primers and complimentary molecules which specifically hybridize to nucleotide sequence that encodes ICEβ, ICEγ, ICEδ and ICEε may be designed routinely by those having ordinary skill in the art.

The present invention also includes labelled oligonucleotides which are useful as probes for performing oligonucleotide hybridization methods to identify ICEβ, ICEγ, ICEδ and ICEε. Accordingly, the present invention includes probes that can be labelled and hybridized to unique nucleotide sequences of ICEβ, ICEγ, ICEδ and ICEε. The labelled probes of the present invention are labelled with radiolabelled nucleotides or are otherwise detectable by readily available nonradioactive detection systems. In some preferred embodiments, probes comprise oligonucleotides consisting of between 10 and 100 nucleotides. In some preferred, probes comprise oligonucleotides consisting of between 10 and 50 nucleotides. In some preferred, probes comprise oligonucleotides consisting of between 12 and 20 nucleotides. The probes preferably contain nucleotide sequence completely identical or complementary to a fragment of a unique nucleotide sequences of ICE62, ICEγ, ICEδ and ICEε.

PCR technology is practiced routinely by those having ordinary skill in the art and its uses in diagnostics are well known and accepted. Methods for practicing PCR technology are disclosed in "PCR Protocols: A Guide to Methods and Applications", Innis, M. A., et al. Eds. Academic Press, Inc. San Diego, Calif. (1990) which is incorporated herein by reference. Applications of PCR technology are disclosed in "Polymerase Chain Reaction" Erlich, H. A., et al., Eds. Cold Spring Harbor Press, Cold Spring Harbor, N.Y. (1989) which is incorporated herein by reference. Some simple rules aid in the design of efficient primers. Typical primers are 18–28 nucleotides in length having 50% to 60% g+c composition. The entire primer is preferably complementary to the sequence it must hybridize to. Preferably, primers generate PCR products 100 basepairs to 2000 base pairs. However, it is possible to generate products of 50 base pairs to up to 10 kb and more.

PCR technology allows for the rapid generation of multiple copies of nucleotide sequences by providing 5' and 3' primers that hybridize to sequences present in a nucleic acid molecule, and further providing free nucleotides and an enzyme which fills in the complementary bases to the nucleotide sequence between the primers with the free nucleotides to produce a complementary strand of DNA. The enzyme will fill in the complementary sequences adjacent to the primers. If both the 5' primer and 3' primer hybridize to nucleotide sequences on the complementary strands of the same fragment of nucleic acid, exponential amplification of a specific double-stranded product results. If only a single primer hybridizes to the nucleic acid molecule, linear amplification produces single-stranded products of variable length.

One having ordinary skill in the art can isolate the nucleic acid molecule that encodes ICEβ, ICEγ, ICEδ and ICEε and insert it into an expression vector using standard techniques and readily available starting materials.

The present invention relates to a recombinant expression vector that comprises a nucleotide sequence that encodes ICEβ, ICEγ, ICEδ or ICEε that comprises the amino acid sequence of SEQ ID NO:4, SEQ ID NO:6, SEQ ID NO:8 and SEQ ID NO:10, respectively. As used herein, the term "recombinant expression vector" is meant to refer to a plasmid, phage, viral particle or other vector which, when introduced into an appropriate host, contains the necessary genetic elements to direct expression of the coding sequence that encodes the ICE isoforms of the invention. The coding sequence is operably linked to the necessary regulatory sequences. Expression vectors are well known and readily available. Examples of expression vectors include plasmids, phages, viral vectors and other nucleic acid molecules or nucleic acid molecule containing vehicles useful to transform host cells and facilitate expression of coding sequences. In some embodiments, the recombinant expression vector comprises the nucleotide sequence set forth in SEQ ID NO:3, SEQ ID NO:5, SEQ ID NO:7 or SEQ ID NO:9. The recombinant expression vectors of the invention are useful for transforming hosts to prepare recombinant expression systems for preparing the ICE isoforms of the invention.

The present invention relates to a host cell that comprises the recombinant expression vector that includes a nucleotide sequence that encodes an ICE isoform that comprises SEQ ID NO:4, SEQ ID NO:6, SEQ ID NO:8 or SEQ ID NO:10. In some embodiments, the host cell comprises a recombinant expression vector that comprises SEQ ID NO:3, SEQ ID NO:5, SEQ ID NO:7 or SEQ ID NO:9. Host cells for use in well known recombinant expression systems for production of proteins are well known and readily available. Examples of host cells include bacteria cells such as E. coli, yeast cells such as S. cerevisiae, insect cells such as S. frugiperda, non-human mammalian tissue culture cells chinese hamster ovary (CHO) cells and human tissue culture cells such as HeLa cells.

The present invention relates to a transgenic non-human mammal that comprises the recombinant expression vector that comprises a nucleic acid sequence that encodes the collagen protein that comprises the amino acid sequence of SEQ ID NO:4, SEQ ID NO:6, SEQ ID NO:8 or SEQ ID NO:10. Transgenic non-human mammals useful to produce recombinant proteins are well known as are the expression vectors necessary and the techniques for generating transgenic animals. Generally, the transgenic animal comprises a recombinant expression vector in which the nucleotide sequence that encodes an ICE isoform of the invention is operably linked to a mammary cell specific promoter whereby the coding sequence is only expressed in mammary cells and the recombinant protein so expressed is recovered from the animal's milk. In some embodiments, the coding sequence that encodes an ICE isoform is SEQ ID NO:3, SEQ ID NO:5, SEQ ID NO:7 or SEQ ID NO:9.

In some embodiments, for example, one having ordinary skill in the art can, using well known techniques, insert such DNA molecules into a commercially available expression vector for use in well known expression systems. For example, the commercially available plasmid pSE420 (Invitrogen, San Diego, Calif.) may be used for production of collagen in E. coli. The commercially available plasmid pYES2 (Invitrogen, San Diego, Calif.) may, for example, be used for production in S. cerevisiae strains of yeast. The commercially available MAXBAC™ complete baculovirus expression system (Invitrogen, San Diego, Calif.) may, for example, be used for production in insect cells. The commercially available plasmid pcDNA I (Invitrogen, San Diego, Calif.) may, for example, be used for production in mammalian cells such as Chinese Hamster Ovary cells. One having ordinary skill in the art can use these commercial expression vectors and systems or others to produce an ICE isoform of the invention using routine techniques and readily available starting materials. (See e.g., Sambrook et al., Molecular Cloning a Laboratory Manual, Second Ed. Cold Spring Harbor Press (1989) which is incorporated herein by reference.) Thus, the desired proteins can be prepared in both prokaryotic and eukaryotic systems, resulting in a spectrum of processed forms of the protein.

One having ordinary skill in the art may use other commercially available expression vectors and systems or produce vectors using well known methods and readily available starting materials. Expression systems containing the requisite control sequences, such as promoters and polyadenylation signals, and preferably enhancers, are readily available and known in the art for a variety of hosts. See e.g., Sambrook et al., Molecular Cloning a Laboratory Manual, Second Ed. Cold Spring Harbor Press (1989).

A wide variety of eukaryotic hosts are also now available for production of recombinant foreign proteins. As in bacteria, eukaryotic hosts may be transformed with expression systems which produce the desired protein directly, but more commonly signal sequences are provided to effect the secretion of the protein. Eukaryotic systems have the additional advantage that they are able to process introns which may occur in the genomic sequences encoding proteins of higher organisms. Eukaryotic systems also provide a variety of processing mechanisms which result in, for example, glycosylation, carboxy-terminal amidation, oxidation or derivatization of certain amino acid residues, conformational control, and so forth.

Commonly used eukaryotic systems include, but is not limited to, yeast, fungal cells, insect cells, mammalian cells, avian cells, and cells of higher plants. Suitable promoters are available which are compatible and operable for use in each of these host types as well as are termination sequences and enhancers, e.g. the baculovirus polyhedron promoter. As above, promoters can be either constitutive or inducible. For example, in mammalian systems, the mouse metallothionein promoter can be induced by the addition of heavy metal ions.

The particulars for the construction of expression systems suitable for desired hosts are known to those in the art. Briefly, for recombinant production of the protein, the DNA encoding the polypeptide is suitably ligated into the expression vector of choice. The DNA is operably linked to all regulatory elements which are necessary for expression of the DNA in the selected host. One having ordinary skill in the art can, using well known techniques, prepare expression vectors for recombinant production of the polypeptide.

The expression vector including the DNA that encodes the ICE isoform is used to transform the compatible host which is then cultured and maintained under conditions wherein expression of the foreign DNA takes place. The protein of the present invention thus produced is recovered from the culture, either by lysing the cells or from the culture medium as appropriate and known to those in the art. One having ordinary skill in the art can, using well known techniques, isolate the ICE isoform that is produced using such expression systems. The methods of purifying ICE isoforms from natural sources using antibodies which specifically bind to the ICE isoform as described above, may be equally applied to purifying ICE isoforms produced by recombinant DNA methodology.

Examples of genetic constructs include the ICE isoform coding sequence operably linked to a promoter that is functional in the cell line into which the constructs are transfected. Examples of constitutive promoters include promoters from cytomegalovirus or SV40. Examples of inducible promoters include mouse mammary leukemia virus or metallothionein promoters. Those having ordinary skill in the art can readily produce genetic constructs useful for transfecting with cells with DNA that encodes ICE isoform from readily available starting materials. Such gene constructs are useful for the production of the ICE isoform.

In some embodiments of the invention, transgenic non-human animals are generated. The transgenic animals according to the invention contain SEQ ID NO:3, SEQ ID NO:5, SEQ ID NO:7 or SEQ ID NO:9 under the regulatory control of a mammary specific promoter. One having ordinary skill in the art using standard techniques, such as those taught in U.S. Pat. No. 4,873,191 issued Oct. 10, 1989 to Wagner and U.S. Pat. No. 4,736,866 issued Apr. 12, 1988 to Leder, both of which are incorporated herein by reference, can produce transgenic animals which produce the ICE isoform. Preferred animals are rodents, particularly goats, rats and mice.

In addition to producing these proteins by recombinant techniques, automated peptide synthesizers may also be employed to produce ICE isoforms of the invention. Such techniques are well known to those having ordinary skill in the art and are useful if derivatives which have substitutions not provided for in DNA-encoded protein production.

ICEε/p20 heterodimers are inactive. ICE activity may be regulated this way, i.e. at the level of formation of ICE heterodimer. The ICEε cDNA codes for a protein which corresponds to the p10 subunit of ICEα except for the first 19 amino acids, which are derived from exon 2 in ICEε, and from exon 7 in the p10 subunit. ICEε, like the p10 subunit, can form a heterodimer with the p20 subunit. The crystal structure of ICEα complexed to a tetrapeptide aldehyde inhibitor suggests that the side chains of p10 residues Val338 to Pro343 interact with the inhibitor, except for Ser339 (Cerretti, D. P., et al. (1992) Science 256, 97–100). Although all these residues are present in ICEε, the ICEε/p20 heterodimer is inactive. This could be attributed to the fact that active ICE exists as a $(p20)_2/(P10)_2$ tetramer in which the participation of p10 residues 318–322 in the formation of this tetrameric complex is essential (Wilson, K. P., et al. (1994) Nature 370, 270–275). Because 4 of these residues are substituted in ICEε, this may prevent the formation of a $(p20)_2/(ICEε)_2$ tetramer.

The biological significance of the expression of an alternatively spliced ICEε isoform is realized from its ability to modulate ICE activity. ICEε might compete with p10 for binding to p20 in vivo. Overexpression of ICEε in Sf9 cells resulted in a delay of apoptosis in a fashion similar to or even better than BCL2 expression. Insect Sf9 cells apparently express an ICE-like protein which might be involved in insect cell apoptosis. Support for the existence of an ICE-like molecule in Sf9 cells was obtained from our overexpression studies of pro-IL-1β. Overexpression of pro-IL-1β in Sf9 cells resulted in its cleavage to the 17.5 kDa active IL-1β cytokine. Three ICE mRNA species (2.5 kb, 1.9 kb and 0.5 kb) have been detected in THP-1 cell line and several other normal human tissues including peripheral blood monocytes, peripheral blood lymphocytes, peripheral blood neutrophils, resting and activated peripheral blood T-lymphocytes and placenta. The smallest 0.5 kb mRNA may be the ICEε isoform. ICEε transcript is highly expressed in peripheral blood neutrophils and placenta. The significance of this high level of expression is not yet established. By acting as a dominant inhibitor, ICEε may inhibit ICE activity thus indirect regulating apoptosis in these tissues.

Accordingly, ICEε may be used as a pharmaceutical to inhibit ICE activity which is involved in both inflammation and apoptosis. Inflammatory diseases include rheumatoid arthritis and Crohn's diseases. Diseases characterized by apoptosis include HIV infection and Alzheimer's disease. Those having ordinary skill in the art can readily identify individuals who are suspected of suffering from such diseases, conditions and disorders using standard diagnostic techniques.

Pharmaceutical compositions according to the invention comprise a pharmaceutically acceptable carrier in combination with an ICE isoform, particularly, ICEδ and ICEε. ICEδ and ICEε function as inhibitors. Pharmaceutical formulations are well known and pharmaceutical compositions comprising ICEε and ICEδ may be routinely formulated by one having ordinary skill in the art. Suitable pharmaceutical carriers are described in Remington's Pharmaceutical Sciences, A. Osol, a standard reference text in this field, which is incorporated herein by reference. The present invention relates to an injectable pharmaceutical composition that comprises a pharmaceutically acceptable carrier and an ICE isoform, particularly, ICEε or ICEδ. Some embodiments of the invention relate to injectable pharmaceutical compositions that comprise a pharmaceutically acceptable carrier and amino acid sequence SEQ ID NO:8 or SEQ ID NO:10. The ICE isoform is preferably sterile and combined with a sterile pharmaceutical carrier.

In some embodiments, for example, ICEε or ICEδ can be formulated as a solution, suspension, emulsion or lyophilized powder in association with a pharmaceutically acceptable vehicle. Examples of such vehicles are water, saline, Ringer's solution, dextrose solution, and 5% human serum albumin. Liposomes and nonaqueous vehicles such as fixed oils may also be used. The vehicle or lyophilized powder may contain additives that maintain isotonicity (e.g., sodium chloride, mannitol) and chemical stability (e.g., buffers and preservatives). The formulation is sterilized by commonly used techniques.

An injectable composition may comprise ICEε and/or ICEδ in a diluting agent such as, for example, sterile water, electrolytes/dextrose, fatty oils of vegetable origin, fatty esters, or polyols, such as propylene glycol and polyethylene glycol. The injectable must be sterile and free of pyrogens.

According to one aspect of the invention, compounds may be screened to identify ICE inhibitors. Since ICE converts IL-1β from an inactive to an active form and IL-1β is associated with inflammation, inhibitors are useful as anti-inflammatory agents. Furthermore, it has been discovered and reported herein that ICE activity is associated with apoptosis. Accordingly, inhibitors of ICE are useful as anti-apoptotic agents.

To screen compounds according to the methods of the present invention, ICEβ or ICEγ is separately combined with proIL-1β in the presence or absence of a test compound. Under assay conditions, the proIL-1β will be processed into active IL-1 in the absence of test compound. Those having ordinary skill in the art can readily detect whether or not proIL-1β has been processed. If proIL-1β is not processed in the presence of the test compound but is processed under the negative control condition in which the test compound is absent, the test compound is an inhibitor of that ICE isoform. Antibodies which inhibit the ICE isoform's activity are useful as inhibitors and, therefore as positive controls in the assay. In some embodiments, ICEα together with ICEβ and ICEγ are each tested to identify ICE inhibitors and to determine if any inhibitors are isoform specific.

Kits are included which comprise containers with reagents necessary to screen test compounds. Such kits include one or more ICE isoforms, including, optionally ICEα together with a substrate such as IL-1β and a means to distinguish processed substrate from uncleaved substrate. Directions for performing the assay are also included in the kit. The means for distinguishing processed substrate from uncleaved substrate include, for example, antibodies which bind to processed substrate but not uncleaved substrate, antibodies which bind to uncleaved substrate but not processed substrate, and liberation assay reagents in labelled uncleaved substrate is bound to solid phase and upon processing of the substrate by the enzyme the label is liberated from the solid phase at which time it is either detected as unbound or its absence is detected from the bound material. Those of ordinary skill in the art can readily design kits to practice the assays of the invention and measure the capacity of test compounds to inhibit ICE isoform activity. Inhibitors are useful as anti-inflammatory and anti-apoptotic agents.

According to another aspect of the invention, ICEδ and ICEε can be used in gene therapy to inhibit ICE activity in several degenerative diseases. By introducing into cells the cDNA that encodes either ICEδ or ICEε in an expressible form, ICEδ or ICEε will be expressed and inhibit ICE activity.

EXAMPLE 1

Materials and Methods

Cloning of ICE Isoforms

The cDNAs for individual ICE isoforms were cloned by a combination of reverse transcription and polymerase chain reaction techniques (RT-PCR). Reverse transcription was performed on poly A+ RNA from the human T-lymphocyte cell line Jurkat or total RNA from the human monocyte cell line THP-1 using a synthetic primer (ICE-RT) derived from the 3' untranslated sequence of human ICE and MuMLV reverse transcriptase. The reverse transcription products were then used as templates for PCR using two nested ICE specific primers ICE1 and ICE2.

Primer sequences were as follows:

ICE-RT, CAGAACGATCTCTTCAC SEQ ID NO:11;
ICE1, ATGGCCGACAAGGTCCTG SEQ ID NO:12; and
ICE2, CCTGCCCGCAGACATTCA SEQ ID NO:13.

The amplified DNA was blunt-ended with T4 DNA polymerase, phosphorylated with T4 polynucleotide kinase and then fractionated on low melting point agarose gels. Several DNA fragments ranging in size from 0.3–1.3 Kb were observed after staining the gel with ethidium bromide. After confirming that all these DNA fragments contain ICE sequences by Southern blot analysis with an ICE specific probe, they were excised from the gel and cloned into a Sma I cut pbluescript II KS+ vector (Stratagene). The cloned cDNAs were then sequenced with T3 and T7 sequencing primers and other ICE specific primers. The largest clone corresponding to the published ICE sequence was designated as KS-ICEα. The other ICE clones were designated as KS-ICEβ, KS-ICEγ, KS-ICEδ and KS-ICEε, based on decreasing size.

Construction of Plasmids, Transfer Vectors and Recombinant Baculoviruses

As outlined above, cDNAs for each individual ICE isoforms were cloned in the Sma I site of pbluescript II KS+ plasmid vector under the T7 promoter. The cDNAs for the p20 and p10 subunits were obtained by PCR using synthetic primers (ICE1 and p20TAA for p20; p10ATG and ICE2 for p10) and KS-ICEγ as a template.

The sequence of the p20TAA primer is GGTTTCCA-GAAACTCCTACTTAATC SEQ ID NO:14 and the p10ATG primer is ATGGCTATTAAGAAAGCCCACATA SEQ ID NO:15.

The amplified DNA fragments were blunt-ended, phosphorylated and then cloned in the Sma I site of pbluescript II KS+ vector under the T7 promoter and designated as KS-p10 and KS-p20. The cDNA fragments corresponding to ICEα, β, γ, δ, ε, p20 and p10 were excised from their corresponding bluescript vectors with Bam HI and Eco RI restriction enzymes and subcloned into a Bam HI/Eco RI cut pVL1393 to generate the corresponding recombinant transfer vectors. These recombinant transfer vectors were then used to generate recombinant baculoviruses.

In vitro Transcription and Translation

The five KS-ICE or KS-p10 vectors were linearized with Eco RI and then used as templates for T7 RNA polymerase. The in vitro synthesized mRNA was precipitated by ethanol, dried and dissolved in TE buffer (10 mM Tris, pH 8.0, 1 mM EDTA). In vitro translation was performed in rabbit reticulocyte lysate in the presence of 80 μCi/ml of $^{35}$S methionine and 200 μg/ml in vitro transcribed mRNA. The translation products were then analyzed by SDS-polyacrylamide gel electrophoresis and autoradiography.

Expression of GST-p20 Fusion Protein in Bacteria

The p20 cDNA was subcloned in frame into the Bam HI site of the bacterial expression vector pGEX-5X-3 (Pharmacia). The p20 cDNA was obtained by PCR using synthetic primers p20GEX and p20TAA and KS-ICEγ as a template.

The sequence of p20GEX primer is GGGATCCTGAAC-CCAGCTATGCCCACATCC SEQ ID NO:16.

The amplified DNA fragment was blunt-ended, phosphorylated and then cloned in the Sma I site of pbluescript II KS+ vector under the T7 promoter. The cDNA fragment was then excised from the bluescript vectors with Bam HI and then subcloned in a Bam HI cut pGEX-5X-3. The expression plasmid PGEX-p20 was introduced into E. coli DH5α and protein expression was induced with IPTG.

Analysis of p20 Interaction with p10 and ICEε

Exponentially growing bacteria carrying the expression plasmid PGEX-p20 was induced with IPTG for 3 h and then lysed by sonication. The recombinant GST-p20 present in the bacterial lysate was adsorbed to glutathione-sepharose resin for 10 min at room temperature and then washed three times with PBS. The immobilized p20 fusion protein was incubated with reticulocyte lysates containing $^{35}$S-labeled p10 or ICEε for 1 h at 30° C. and then washed five times with PBS containing 0.1% Triton X-100. Laemmli sample buffer was then added to the resin and the eluted proteins were analyzed on a 5–20% SDS-polyacrylamide gradient gel and visualized by autoradiography.

Results

Cloning of Four Novel ICE Isoforms

Employing RT-PCR to analyze the expression of ICE mRNA in the human Jurkat T-lymphocyte cell line, several DNA products of 1248, 1185, 969, 825 and 300 bp were detected by ethidium bromide staining. The two largest PCR products were the most abundant. All five products were detected by Southern blot hybridization using the full length ICE cDNA as a probe. This pattern of RT-PCR products was also observed using total RNA from the human acute monocytic leukemia cell line THIP-1. Subsequently, the two largest PCR products (1185 and 1248 bp) were cloned from Jurkat mRNA and the three smaller less abundant products (300, 825 and 969 bp) which represent 10–15% of the larger products were cloned from THP-1 mRNA. All cloned PCR products were then sequenced. The largest form (1248 bp) corresponds to the sequence of the full length ICE as reported previously and was designated as ICEδ. Intriguingly, sequence analysis of the four smaller PCR products revealed that these forms were generated by independent alternative splicing events of the parental ICE mRNA transcript. Table I lists the deletion sizes in the isoforms and the amino acid interrupted due to the splice. Table II lists the splice donor and acceptor sequences of the human ICE gene that are utilized to generate the four ICE isoforms. All the splice junction sequences within the splice donor and acceptor sites conform to the consensus GT/AG rule.

The 1185 bp cDNA, designated as ICEβ lacks the entire exon 3 of the ICE gene (bp 275 to 338; a.a 92–112).

The 969 bp cDNA, designated as ICEγ, lacks most of exon 2 and the entire exon 3 (bp 59 to 338; a.a 20–112).

The 825 bp cDNA, designated as ICEδ is similar to ICEγ but also lacks the entire exon 7 (bp 863 to 1006; a.a 288–335).

The smallest 300 bp cDNA, designated as ICEε lacks most of exon 2 and exons 3 to 7 (bp 59 to 1006; a.a 20–335).

All these alternatively spliced ICE isoforms maintained an open reading frame which gave rise to different translation products. ICE proenzyme (ICEα here) requires proteolytic cleavage to generate p20 and p10 subunits for enzymatic activation. It is not yet clear whether ICE activation occurs via an intramolecular autoprocessing mechanism or requires limited proteolysis by an unknown protease. However, it has been shown that active ICE heterodimer can cleave reticulocyte lysate translated proICE to generate the p20 and p10 subunits. Because ICE isoforms β, γ and δ contain the active site Cys285 but lack part or most of the 119 N-terminal propeptide it was interesting to determine whether these isoforms possess autoprocessing activity.

ICE isoforms α, β, γ and δ were in vitro transcribed and translated in rabbit reticulocyte lysates. Translation of ICE mRNA isoforms gave rise to 30–48 kDa translation products. A major 34 kDa product in ICEα and ICEβ translation reactions was also detected. This p34 product is similar in size to the ICEγ translation product and could be a processed ICEα and β. However, all these products were stable for 24 h in reticulocyte lysates at room temperature. No decrease in the intensity of the 30–48 kDa translation products or appearance of a p20 species was observed after this prolonged incubation. In addition, incubation of ICEα with ICEγ or ICE62, or incubation of ICEγ with ICEδ for 24 h at room temperature did not result in processing of these isoforms to the p20 and p10 subunits. The stability of the ICE isoforms suggests that ICE isoforms do not possess autocatalytic activity under these in vitro conditions.

Determination of the Apoptotic Activity of ICE Isoforms

To determine the ability of the individual ICE isoforms to induce apoptosis, each ICE isoform was overexpressed in *Spodoptera frugiperda* (Sf9) cells with the baculovirus system. The viability of infected cells was determined at various times postinfection. The viability of Sf9 cells infected with the recombinant ICEα baculovirus decreased sharply 24–48 h postinfection. Similar effects were also observed with ICEβ and ICEγ. In contrast, cells infected with the wild type virus, ICEδ, ICEε, or BCL2 baculoviruses showed very little decrease in viability during this period.

The decrease in viability of cells infected with the recombinant ICEα, β and γ baculoviruses was due to induction of apoptosis when the recombinant ICE proteins started to rise 24–48 h postinfection. This period is the time at which proteins under the polyhedrin promoter are induced. During this period, cells expressing ICEα, β or γ showed characteristic signs of apoptosis including cytoplasmic membrane blebbing, nuclear condensation and internucleosomal DNA cleavage. These apoptotic signs were not observed in Sf9 cells infected with ICEδ or ε, baculoviruses or with the wild type or BCL2 baculoviruses (Alnemri, E. S., et al. (1992) *Proc. Natl. Acad. Sci. USA* 89, 7295–7299). In fact, it was surprising to discover that expression of ICEε and to a lesser degree ICEδ conferred some protection and delayed the apoptotic response to baculovirus infection.

In this experiment, cells infected with ICEε baculovirus showed a lesser decrease in viability compared to cells infected with the wild type virus. This protective effect was similar to that observed with the expression of BCL2 in these cells. Coexpression of ICEα with BCL2 or ICEε resulted in a slight delay in the onset of apoptosis, but was not protective. Because of the lethality of ICEα, a significantly lower expression of BCL2 or ICEε was detected in this coexpression experiment.

Because ICEε is homologous to the p10 subunit of active ICE, its coexpression with the p20 subunit was tested to determine whether could generate an active ICE heterodimer. The results of these experiments showed that expression of either the p10, p20 or ICEε in Sf9 cells does not cause apoptosis. On the other hand, coexpression of the p10 and p20 subunits resulted in apoptosis within the same time frame as did ICEα. In contrast, coexpression of ICEε and p20 does not cause apoptosis in Sf9 cells. These results suggest that the first 19 amino acids of the p10 subunit are essential for ICE activity. Substitution of these amino acids as in ICEε may result in loss of activity.

Determination of the Ability of ICEε to Interact with p20

To determine whether ICEε can interact with p20, ICEε was in vitro transcribed and then translated in reticulocyte lysate in the presence of $^{35}S$ methionine. The labeled ICEε was then incubated with a GST-p20 fusion protein expressed in bacteria and immobilized on glutathione-sepharose resin. The p10 subunit was also labeled in reticulocyte lysate with $^{35}S$ and used as a control. Both p10 and ICEε were able to interact with the GST-p20 fusion protein. A small amount of p10 and ICEε were bound nonspecifically to free glutathione-sepharose resin. These results suggest that ICEε can form a heterodimer with p20 and may regulate its activity in vivo by forming an inactive complex.

TABLE I

Deletion in ICE isoforms. The size of deletions refer to the number of base pairs deleted in the respective splice variants. Also listed is the amino acid interrupted by the splice.

| Isoform | Size of deletion (bp) | Amino acid interrupted |
|---|---|---|
| β | 63 | Asp92 |
| γ | 179 | Gly20 |
| δ | 143 | Asp288 |
| ε | 957 | Gly20 |

TABLE II

Splice junction sequences in ICE isoforms. The intron sequences at the splice junctions are represented in lowercase. The exon sequences at the splice junctions and the exon 2 sequence used as the internal splice donor in ICE γ, δ and ε are represented in uppercase.

| Isoform | Donor | Acceptor |
|---|---|---|
| β | GCA G gtaagggtca . . . tctcttgcag CT CCT | (SEQ ID NO:17) |
| γ | GAA G GTACAATAAA . . . tctcttgcag CT CCT | (SEQ ID NO:18) |
| δ | GGT G gtgagtgctg . . . ttatccatag AT AAT | (SEQ ID NO:20) |
| ε | GAA G GTACAATAAA . . . ttatccatag AT AAT | (SEQ ID NO:21) |
| β | GCAGCTCCT | (SEQ ID NO:22) |
| γ | GAAGGTACAATAAACTCCT | (SEQ ID NO:23) |
| δ | GGTGATAAT | (SEQ ID NO:24) |
| ε | GAAGGTACAATAAAATAAT | (SEQ ID NO:25) |

We claim:

1. An isolated nucleic acid molecule consisting of a nucleotide sequence selected from the group consisting of: SEQ ID NO: 3, SEQ ID NO: 5, SEQ ID NO: 7 and SEQ ID NO:9.

2. A recombinant expression vector comprising a nucleic acid sequence that encodes the protein having an amino acid sequence selected from the group consisting of: SEQ ID NO:4, SEQ ID NO:6, SEQ ID NO:8 and SEQ ID NO:10.

3. A host cell comprising the recombinant expression vector of claim 2.

4. A recombinant expression vector comprising the nucleic acid molecule of claim 1.

5. A host cell comprising the recombinant expression vector of claim 4.

6. An isolated nucleic acid molecule according to claim 8 consisting of SEQ ID NO:3.

7. An isolated nucleic acid molecule according to claim 1 consisting of SEQ ID NO:5.

8. An isolated nucleic acid molecule according to claim 1 consisting of SEQ ID NO:7.

9. An isolated nucleic acid molecule according to claim 8 consisting of SEQ ID NO:9.

10. A recombinant expression vector according to claim 2 comprising a nucleic acid sequence that encodes the protein having the amino acid sequence of SEQ ID NO:4.

11. A recombinant expression vector according to claim 2 comprising a nucleic acid sequence that encodes the protein having the amino acid sequence of SEQ ID NO:6.

12. A recombinant expression vector according to claim 2 comprising a nucleic acid sequence that encodes the protein having the amino acid sequence of SEQ ID NO:8.

13. A recombinant expression vector according to claim 2 comprising a nucleic acid sequence that encodes the protein having the amino acid sequence of SEQ ID NO:10.

14. An isolated nucleic acid molecule consisting of up to a total of 50 nucleotides including a nucleotide sequence selected from the group consisting of SEQ ID NO:22, SEQ ID NO:23, SEQ ID NO;24 and SEQ ID NO:25.

15. An isolated nucleic acid molecule consisting of up to a total of 100 nucleotides including a nucleotide sequence of SEQ ID NO:22. therein said nucleic acid molecule is a fragment of a nucleic acid molecule having SEQ ID NO:3.

16. An isolated nucleic acid molecule consisting of up to a total of 50 nucleotides including a nucleotide sequence of SEQ ID NO:22, wherein said nucleic acid molecule is a fragment of a nucleic acid molecule having SEQ ID No:3.

17. An isolated nucleic acid molecule consisting of up to a total of 100 nucleotides including a nucleotide sequence of SEQ ID NO:23, wherein said nucleic acid molecule is a fragment of a nucleic acid molecule having SEQ ID NO:5.

18. An isolated nucleic acid molecule of up to a total of 50 nucleotides including a nucleotide sequence selected from the group consisting of SEQ ID NO:23, wherein said nucleic acid molecule is a fragment of a nucleic acid molecule having SEQ ID NO:5.

19. An isolated nucleic acid molecule consisting of up to a total of 100 nucleotides including a nucleotide sequence of SEQ ID NO:24, wherein said nucleic acid molecule is a fragment of a nucleic acid molecule having SEQ ID NO:7.

20. An isolated nucleic acid molecule consisting of up to a total of 50 nucleotides including a nucleotide sequence of SEQ ID NO:24, wherein said nucleic acid molecule is a fragment of a nucleic acid molecule having SEQ ID NO:7.

21. An isolated nucleic acid molecule consisting of up to a total of 100 nucleotides including a nucleotide sequence of SEQ ID NO:25, wherein said nucleic acid molecule is a fragment of a nucleic acid molecule having SEQ ID NO:9.

22. The isolated nucleic acid molecule consisting of up to a total of 50 nucleotides including a nucleotide sequence of SEQ ID NO:25, wherein said nucleic acid molecule is a fragment of a nucleic acid molecule having SEQ ID NO:9.

23. An isolated nucleic acid molecule consisting of up to a total of 100 nucleotides including a nucleotide sequence of SEQ ID NO:22.

24. An isolated nucleic acid molecule consisting of up to a total of 100 nucleotides including a nucleotide sequence of SEQ ID NO:23.

25. An isolated nucleic acid molecule consisting of up to a total of 58 nucleotides including a nucleotide sequence of SEQ ID NO:24.

26. An isolated nucleic acid molecule consisting of up to a total of 100 nucleotides including a nucleotide sequence of SEQ ID NO:25.

27. A PCR primer of up to 58 nucleotides comprising a nucleotide sequence identical or complementary to a nucleotide sequence of SEQ ID NO:24.

28. A PCR primer of up to 100 nucleotides comprising a nucleotide sequence identical or complementary to a nucleotide sequence selected from the group consisting of SEQ ID NO:22, SEQ ID NO:23 and SEO ID NO:25.

29. The PCR primer of claim 28 comprising a nucleotide sequence identical or complementary to SEQ ID NO:22.

30. The PCR primer of claim 28 comprising a nucleotide sequence identical or complementary to SEQ ID NO:23.

31. The PCR primer of claim 28 comprising a nucleotide sequence identical or complementary to SEQ ID NO: 25.

* * * * *